United States Patent
Stanford et al.

(10) Patent No.: US 11,260,116 B2
(45) Date of Patent: Mar. 1, 2022

(54) VACCINE COMPOSITIONS COMPRISING AN AMPHIPATHIC COMPOUND, A NEOANTIGEN AND A HYDROPHOBIC CARRIER, AND METHODS OF USE THEREOF

(71) Applicant: IMMUNOVACCINE TECHNOLOGIES INC., Dartmouth (CA)

(72) Inventors: Marianne Stanford, Nova Scotia (CA); Genevieve Weir, Halifax (CA); Frederic Ors, Quebec (CA); Leeladhar Sammatur, Irvine, CA (US)

(73) Assignee: IMMUNOVACCINE TECHNOLOGIES INC., Dartmouth (CA)

( * ) Notice: Subject to any disclaimer, the term of this patent is extended or adjusted under 35 U.S.C. 154(b) by 307 days.

(21) Appl. No.: 16/098,042

(22) PCT Filed: May 3, 2017

(86) PCT No.: PCT/CA2017/050539
§ 371 (c)(1),
(2) Date: Oct. 31, 2018

(87) PCT Pub. No.: WO2017/190242
PCT Pub. Date: Nov. 9, 2017

(65) Prior Publication Data
US 2019/0151428 A1    May 23, 2019

Related U.S. Application Data

(60) Provisional application No. 62/331,770, filed on May 4, 2016.

(51) Int. Cl.
| | | |
|---|---|---|
| A61K 39/00 | (2006.01) | |
| C07K 14/47 | (2006.01) | |
| C07K 14/705 | (2006.01) | |
| A61P 35/00 | (2006.01) | |
| A61K 39/39 | (2006.01) | |
| A61K 45/06 | (2006.01) | |

(52) U.S. Cl.
CPC ...... *A61K 39/001114* (2018.08); *A61K 39/00* (2013.01); *A61K 39/0011* (2013.01); *A61K 39/39* (2013.01); *A61K 45/06* (2013.01); *A61P 35/00* (2018.01); *C07K 14/47* (2013.01); *C07K 14/705* (2013.01); *A61K 2039/55516* (2013.01); *A61K 2039/55555* (2013.01); *A61K 2039/55561* (2013.01); *A61K 2039/55566* (2013.01); *A61K 2039/55572* (2013.01)

(58) Field of Classification Search
None
See application file for complete search history.

(56) References Cited

U.S. PATENT DOCUMENTS

2015/0224182 A1*  8/2015  Hunt .............. A61K 39/001182
                                                      424/85.2

FOREIGN PATENT DOCUMENTS

| WO | 2002038175 A1 | 5/2002 | |
|---|---|---|---|
| WO | 2009043165 A1 | 4/2009 | |
| WO | WO 2009/043165 * | 4/2009 | ............ A61K 39/39 |
| WO | 2012159754 A2 | 11/2012 | |
| WO | 2014082729 A1 | 6/2014 | |
| WO | WO 2014/082729 * | 6/2014 | ............ A61K 39/00 |
| WO | 2014153636 A1 | 10/2014 | |
| WO | 2015123496 A1 | 8/2015 | |
| WO | 2016176761 A1 | 11/2016 | |

OTHER PUBLICATIONS

Supplementary European Search Report dated Nov. 28, 2019, issued in corresponding Application No. PCT/CA2017/050539.
Karkada, M. et al., "A Novel Breast Ovarian Cancer Peptide Vaccine Platform That Promotes Specific Type-1 but not Treg/Tr1-type Responses", J. Immunotherapy, vol. 33, No. 3, pp. 250-261 (2010). XP008152974.
International Search Report and Written Opinion dated Jul. 26, 2017, issued in corresponding Application No. PCT/CA2017/050539.
Castle et al., "Exploiting the Mutanome for Tumor Vaccination", Cancer Research, 2012, vol. 72, No. 5, pp. 1081-1091.

* cited by examiner

*Primary Examiner* — Nelson B Moseley, II
(74) *Attorney, Agent, or Firm* — Troutman Pepper Hamilton Sanders LLP

(57) ABSTRACT

The present application relates to vaccine compositions comprising an amphipathic compound, a neoantigen and a hydrophobic carrier. Further described are methods and use of the vaccine composition for inducing an antibody immune response and/or a cell-mediated immune response to the neoantigen, as well as methods and uses of the vaccine compositions in the treatment of cancer.

22 Claims, 3 Drawing Sheets

Specification includes a Sequence Listing.

SEQUENCE LISTING

```
<160> NUMBER OF SEQ ID NOS: 9

<210> SEQ ID NO 1
<211> LENGTH: 16
<212> TYPE: PRT
<213> ORGANISM: Artificial Sequence
<220> FEATURE:
<223> OTHER INFORMATION: T-helper epitope from tetanus toxoid peptide
      (A16L)

<400> SEQUENCE: 1

Ala Gln Tyr Ile Lys Ala Asn Ser Lys Phe Ile Gly Ile Thr Glu Leu
1               5                   10                  15

<210> SEQ ID NO 2
<211> LENGTH: 27
<212> TYPE: PRT
<213> ORGANISM: Artificial Sequence
<220> FEATURE:
<223> OTHER INFORMATION: Mut30 Neoantigen

<400> SEQUENCE: 2

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu
            20                  25

<210> SEQ ID NO 3
<211> LENGTH: 20
<212> TYPE: DNA
<213> ORGANISM: Artificial Sequence
<220> FEATURE:
<223> OTHER INFORMATION: CpG Oligonucleotide

<400> SEQUENCE: 3
tccatgacgt tcctgacgtt                                                  20

<210> SEQ ID NO 4
<211> LENGTH: 6
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM2 or PAM3

<400> SEQUENCE: 4

Cys Ser Leu Leu Leu Leu
1               5

<210> SEQ ID NO 5
<211> LENGTH: 26
<212> TYPE: DNA
<213> ORGANISM: Artificial Sequence
<220> FEATURE:
<223> OTHER INFORMATION: 26-mer single-stranded polyI:C
<220> FEATURE:
```

<221> NAME/KEY: Modified_base
<222> LOCATION: (1)..(1)
<223> OTHER INFORMATION: Inosine
<220> FEATURE:
<221> NAME/KEY: Modified_base
<222> LOCATION: (3)..(3)
<223> OTHER INFORMATION: Inosine
<220> FEATURE:
<221> NAME/KEY: Modified_base
<222> LOCATION: (5)..(5)
<223> OTHER INFORMATION: Inosine
<220> FEATURE:
<221> NAME/KEY: Modified_base
<222> LOCATION: (7)..(7)
<223> OTHER INFORMATION: Inosine
<220> FEATURE:
<221> NAME/KEY: Modified_base
<222> LOCATION: (9)..(9)
<223> OTHER INFORMATION: Inosine
<220> FEATURE:
<221> NAME/KEY: Modified_base
<222> LOCATION: (11)..(11)
<223> OTHER INFORMATION: Inosine
<220> FEATURE:
<221> NAME/KEY: Modified_base
<222> LOCATION: (13)..(13)
<223> OTHER INFORMATION: Inosine
<220> FEATURE:
<221> NAME/KEY: Modified_base
<222> LOCATION: (15)..(15)
<223> OTHER INFORMATION: Inosine
<220> FEATURE:
<221> NAME/KEY: Modified_base
<222> LOCATION: (17)..(17)
<223> OTHER INFORMATION: Inosine
<220> FEATURE:
<221> NAME/KEY: Modified_base
<222> LOCATION: (19)..(19)
<223> OTHER INFORMATION: Inosine
<220> FEATURE:
<221> NAME/KEY: Modified_base
<222> LOCATION: (21)..(21)
<223> OTHER INFORMATION: Inosine
<220> FEATURE:
<221> NAME/KEY: Modified_base
<222> LOCATION: (23)..(23)
<223> OTHER INFORMATION: Inosine
<220> FEATURE:
<221> NAME/KEY: Modified_base
<222> LOCATION: (25)..(25)
<223> OTHER INFORMATION: Inosine

<400> SEQUENCE: 5
ncncncncnc ncncncncnc ncncnc                                       26

<210> SEQ ID NO 6
<211> LENGTH: 13
<212> TYPE: PRT
<213> ORGANISM: Artificial Sequence
<220> FEATURE:
<223> OTHER INFORMATION: PADRE T-helper epitope
<220> FEATURE:
<221> NAME/KEY: Misc_feature
<222> LOCATION: (3)..(3)
<223> OTHER INFORMATION: Xaa may be cyclohexylalanyl

<400> SEQUENCE: 6

Ala Lys Xaa Val Ala Ala Trp Thr Leu Lys Ala Ala Ala
1               5                   10

<210> SEQ ID NO 7
<211> LENGTH: 21
<212> TYPE: PRT
<213> ORGANISM: Artificial Sequence
<220> FEATURE:

```
<223> OTHER INFORMATION: T-helper epitope from tetanus toxoid peptide
      (F21E)

<400> SEQUENCE: 7

Phe Asn Asn Phe Thr Val Ser Phe Trp Leu Arg Val Pro Lys Val Ser
1               5                   10                  15

Ala Ser His Leu Glu
            20

<210> SEQ ID NO 8
<211> LENGTH: 9
<212> TYPE: PRT
<213> ORGANISM: Artificial Sequence
<220> FEATURE:
<223> OTHER INFORMATION: Irrelevant peptide (R9F)

<400> SEQUENCE: 8

Arg Ala His Tyr Asn Ile Val Thr Phe
1               5

<210> SEQ ID NO 9
<211> LENGTH: 9
<212> TYPE: PRT
<213> ORGANISM: Artificial Sequence
<220> FEATURE:
<223> OTHER INFORMATION: Irrelevant peptide

<400> SEQUENCE: 9

Glu Gly Pro Arg Asn Gln Asp Trp Leu
1               5
```

VACCINE COMPOSITIONS COMPRISING AN AMPHIPATHIC COMPOUND, A NEOANTIGEN AND A HYDROPHOBIC CARRIER, AND METHODS OF USE THEREOF

CROSS-REFERENCE TO RELATED PATENT APPLICATIONS

This application is a U.S. National Phase of International Patent Application. PCT/CA2017/050539, filed May 3, 2017, which claims priority to U.S. Provisional Application No. 62/331,770, filed May 4, 2016, the disclosure of each of which is herein incorporated by reference in their entirety.

FIELD

The present application relates to vaccine compositions comprising an amphipathic compound, a neoantigen and a hydrophobic carrier, and methods of using such compositions in the treatment of cancer.

BACKGROUND

In immunotherapy, and cancer immunotherapy in particular, generating sufficiently potent immune responses is a major obstacle. The immune responses to cancer vaccine antigens are often hampered by immune tolerance mechanisms, which originate within the tumor as a mechanism of immune escape (Kim 2007). Moreover, highly purified and synthetic antigens, such as peptides, are often poorly immunogenic and thus require immune stimulants such as adjuvants to facilitate robust immune responses (Irvine 2013).

Neoantigens are emerging as a very strong option to advance personalized cancer medicine, as they have tremendous potential to effect cancer treatments that provide truly individualized immunotherapies; however, suitable delivery platforms are still required (Mullard 2016).

Neoantigens are the result of mutations in the somatic DNA of tumors and, as such, represent a form of personalized therapy. In contrast to shared tumor antigens which are selectively expressed or over-expressed in tumors in many individuals (but still may be expressed in normal cells), neoantigens contain tumor-specific and/or patient-specific mutations and have the potential to uniquely mark a tumor for destruction while avoiding self-tolerance.

As a result of these and other mutations or modifications, neoantigens contain predicted epitopes (B cell and T cell) that are unique to each patient. Neoantigens, and the neoepitopes contained therein, may or may not be immunogenic when injected as a vaccine, therefore selecting the appropriate formulation for immunization is crucial for ensuring optimal immunogenicity. Additionally, since each peptide pool is unique to each patient, the process of identifying and then formulating the neoantigens and/or neoepitopes into an appropriate vaccine formulation within a reasonable time frame is a significant consideration in respect of their ultimate use in patient therapy. Each peptide pool will contain different peptides with different properties which may require optimization, particularly if the vaccine formulation is not sufficient to handle weakly immunogenic antigens.

There remains a need for the development of optimal vaccine compositions for inducing strong humoral and/or cell-mediated immune responses against neoantigens. In the present disclosure, we describe novel vaccine compositions for enhancing immunogenicity against neoantigens, including neoantigens which are weakly immunogenic.

SUMMARY

In an embodiment, the present invention relates to a vaccine composition comprising: (a) an amphipathic compound; (b) a neoantigen; and (c) a hydrophobic carrier.

In another embodiment, the vaccine composition as described herein is water-free or substantially free of water.

In another embodiment, the present invention relates to a vaccine composition which comprises: (a) a lipid molecule mixture of 1,2-dioleoyl-sn-glycero-3-phosphocholine (DOPC) and cholesterol; (b) a neoantigen; (c) the hydrophobic carrier Montanide® ISA 51; (d) a universal T-helper epitope from tetanus toxoid comprising the amino acid sequence AQYIKANSKFIGITEL (A16L peptide; SEQ ID NO: 1); and (e) a DNA and/or RNA polyI:C polynucleotide adjuvant.

In another embodiment, the present invention relates to a method comprising administering the vaccine composition as described herein to a subject in need thereof. In an aspect of this embodiment, the method is for inducing an antibody immune response and/or a cell-mediated immune response to the neoantigen in the subject. In another aspect of this embodiment, the method is for the treatment and/or prevention of cancer.

In another embodiment, the method as described herein further comprises administering to the subject an agent that interferes with DNA replication, such as for example cyclophosphamide.

In another embodiment, the method as described herein further comprises administering to the subject an immune response checkpoint inhibitor, such as for example an inhibitor of Programmed Death-Ligand 1 (PD-L1), Programmed Death 1 (PD-1), CTLA-4, PD-L2, LAG3, TIM3, 41BB, 2B4, A2aR, B7H1, B7H3, B7H4, BTLA, CD2, CD27, CD28, CD30, CD40, CD70, CD80, CD86, CD160, CD226, CD276, DR3, GALS, GITR, HVEM, IDO1, IDO2, inducible T cell costimulatory (ICOS), KIR, LAIR1, LIGHT, macrophage receptor with collageneous structure (MARCO), phosphatidylserine (PS), OX-40, SLAM, TIGIT, VISTA, VTCN1, or any combination thereof.

In another embodiment, the present invention relates to the use of a composition as described herein for inducing an antibody immune response to said neoantigen in a subject.

In another embodiment, the present invention relates to the use of a composition as described herein for inducing a cell-mediated immune response to said neoantigen in a subject.

In another embodiment, the present invention relates to the use of a composition as described herein for the treatment and/or prevention of cancer.

In another embodiment, the present invention relates to a kit comprising: a first container comprising an amphipathic compound and a neoantigen; and a second container comprising a hydrophobic carrier.

BRIEF DESCRIPTION OF THE FIGURES

In the figures, which illustrate embodiments of the invention by way of example only.

DETAILED DESCRIPTION

Figure 1:
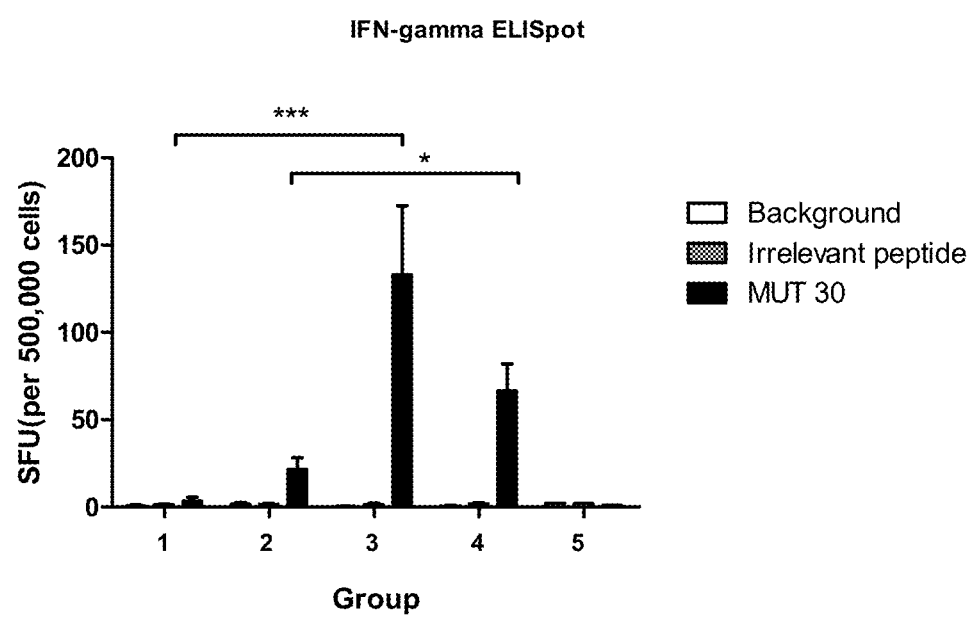
FIG. 1 illustrates the IFN-gamma ELISPOT responses of C57BL/6 VAF/Elite® Crl mice vaccinated with Mut30 antigen prepared in either an oil-based formulation or an aqueous formulation. Immune responses were measured eight days after vaccination by stimulating splenocytes with syngeneic dendritic cells unloaded or loaded with an irrelevant peptide or Mut 30 neoantigen in an IFN-gamma ELISPOT plate. Statistical analysis was performed by 2-way ANOVA with Bonferroni post test comparing group responses to Mut30 peptide: *p<0.05, ***p<0.001.

One of the critical barriers in finding an effective treatment against constantly mutating cancer cells and epitopes has been the inability to rapidly identify neoantigens (or mutated epitopes thereof), synthesize them as peptides and manufacture these peptides in a suitable formulation to deliver as a personalized vaccine to a patient. Ideally, for a personalized medicine, this entire process could be accomplished in about 6 to 8 weeks.

Some hurdles include, for example, (i) the absence of technologies to rapidly identify neoantigens and/or their neoepitopes, (ii) the identification of a vaccine composition that can be produced in a rapid and cost-effective manner for a production scale as small as one patient, e.g. for personalized medicine, (iii) the identification of a suitable vaccine composition (e.g. delivery platform) that generates sufficiently strong and specific immune responses against a neoantigen, preferably after a single administration and with low doses of the neoantigen to avoid cross-reactivity, (iv) the ability of the vaccine composition to effectively deliver long peptide antigens (e.g. greater than 25 amino acids in length), (v) the identification of a vaccine composition that is suitable to generate an immune response (e.g. a CTL immune response) against multiple peptide neoantigens targeting multiple epitopes across a broad range of epitopes, and (vi) the ability of the vaccine composition to induce potent immune responses to neoantigens or neoepitopes that have not been selected for their proven ability to be strongly immunogenic and are apt to be weakly immunogenic.

In view of these hurdles, the importance of a vaccine composition having the ability to improve the immunogenicity of a neoantigen is significantly greater than in traditional vaccine epitope selection. Moreover, it is desirable that the vaccine composition be capable of inducing an effective immune response against multiple epitopes at the same time using peptide neoantigens. It is also desirable that the vaccine composition be capable of inducing an immune response to a low dose of the neoantigen after only a single administration, with the aim of avoiding cross-reactivity against the wild-type peptide in the subject.

Described in the present application are vaccine compositions that are capable of inducing potent immune responses, even in respect of weakly immunogenic neoantigens. Moreover, the vaccine compositions as disclosed herein should be compatible and amenable to cost-effective, scalable manufacturing capabilities.

The oil-based compositions of the invention, comprising an amphipathic compound; a neoantigen; and a hydrophobic carrier, were surprisingly capable of generating statistically significant enhanced immune responses to a neoantigen peptide after single administration, as compared to equivalent aqueous-based formulations.

As an exemplary neoantigen, we used the Mut30 neoantigen identified by Castle 2012. Castle 2012 purport that the Mut30 neoantigen was capable of generating strong mutation-specific immune responses in mice using an aqueous-based composition. However, Castle 2012 did not study low dose administration of Mut30 with only a single administration, which may represent important features of a successful neoantigen vaccine, particularly for weakly immunogenic neoantigens where high doses or repeated administration could lead to cross-reactivity with self-peptides.

Figure 3:
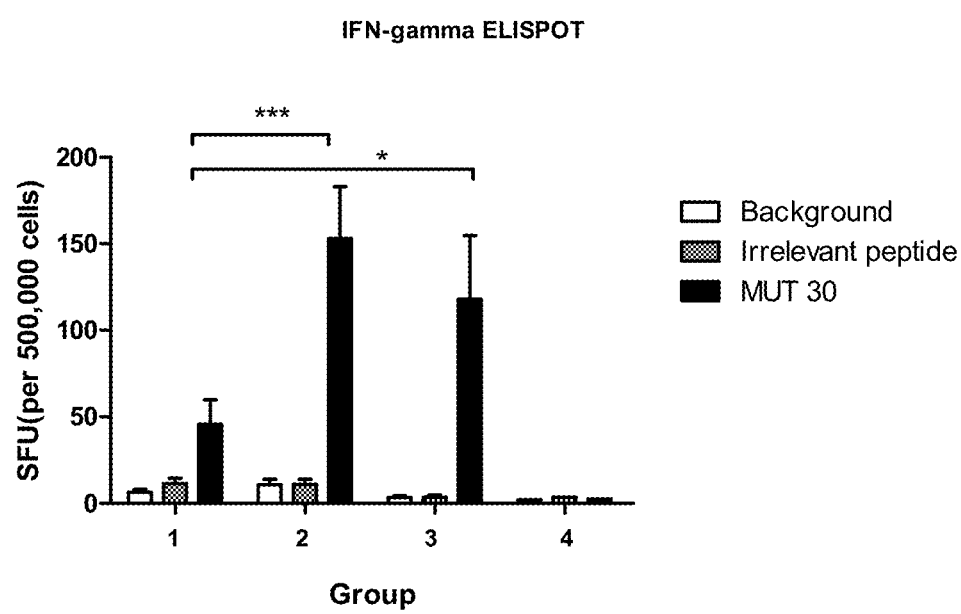
FIG. 3 illustrates the IFN-gamma ELISPOT responses of C57BL/6NCrl mice vaccinated with Mut30 neoantigen prepared with RNA or DNA based polyI:C molecule in either an oil-based formulation or an aqueous buffered formulation. Immune responses were measured eight days after vaccination by stimulating splenocytes with syngeneic dendritic cells unloaded or loaded with an irrelevant peptide or Mut 30 neoantigen in an IFN-gamma ELISPOT plate. Statistical analysis was performed by 2-way ANOVA with Bonferroni post test comparing group responses to Mut30 peptide, *p<0.05, ***p<0.001.

As shown herein, we were unable to generate strong immune responses with aqueous-based formulations comprising a Mut30 neoantigen after single administration. In contrast, when the Mut30 neoantigen was formulated in the oil-based compositions of the invention, the immune responses were significantly enhanced. These results are shown in FIGS. 1 and 3. The oil-based compositions of the invention were capable of generating cell-mediated immune responses against the 27-amino acid Mut30 neoantigen peptide at levels that were consistently at least about 3-fold greater than with the aqueous-based formulations after a single administration. This is a surprising result given that neoantigens are often weakly immunogenic peptides.

Figure 2:
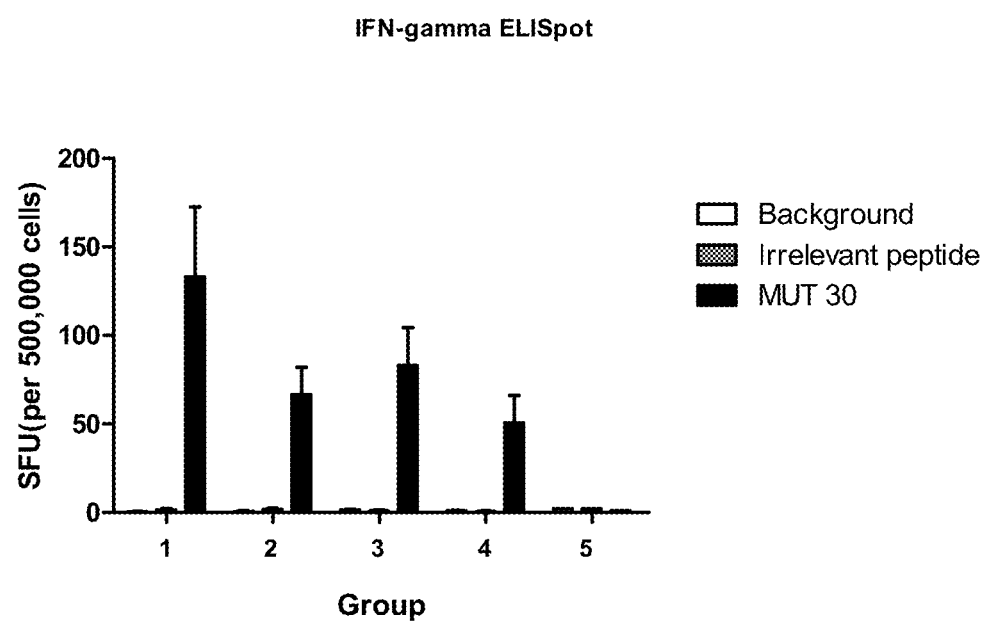
FIG. 2 illustrates the IFN-gamma ELISPOT responses of C57BL/6 VAF/Elite® Crl mice vaccinated with Mut30 neoantigen prepared at different doses in an oil-based formulation. Immune responses were measured eight days after vaccination by stimulating splenocytes with syngeneic dendritic cells unloaded or loaded with an irrelevant peptide or Mut 30 neoantigen in an IFN-gamma ELISPOT plate. Statistical analysis was performed by 2-way ANOVA with Bonferroni post test comparing group responses to Mut30 peptide.

Moreover, the oil-based formulations of the invention were able to generate these enhanced immune responses with significantly lower doses of the neoantigen. As shown in FIG. 2, the oil-based compositions of the invention were capable of generating comparable immune responses to the Mut30 neoantigen at both high and low doses of 100 micrograms and 50 micrograms, respectively. Given the similarity between neoantigens and self-peptides (e.g. single amino acid mutations), the ability to reduce the amount of neoantigen delivered, while still providing an effective immune response, represents an important advantage of the present invention.

It is clear from the examples described herein that the compositions of the invention are capable of inducing unusually strong immune responses to neoantigens, at low dose amounts after single administration.

Vaccine Compositions

In an embodiment, the present disclosure relates to a vaccine composition comprising an amphipathic compound, a neoantigen and a hydrophobic carrier. Each of these components is individually described herein in greater detail. In an embodiment, the vaccine composition is water-free or substantially free of water as described herein.

As used herein, the terms "vaccine", "vaccine composition" or "composition" may be used interchangeably, as the context requires.

Vaccine compositions as disclosed herein may be administered to a subject in a therapeutically effect amount. As used herein, a "therapeutically effective amount" means an amount of the vaccine or active ingredient (e.g., one or more neoantigens) effective to stimulate, induce, maintain, boost or enhance an immune response in a subject. In some embodiments, a therapeutically effective amount of the vaccine is an amount capable of inducing a clinical response in a subject in the treatment of a particular disease or disorder. Determination of a therapeutically effective amount of the vaccine is well within the capability of those skilled in the art, especially in light of the disclosure provided herein. The therapeutically effective amount may vary according to a variety of factors such as the subject's condition, weight, sex and age.

Neoantigen

The vaccine compositions as disclosed herein comprise one or more neoantigens.

As used herein, the term "neoantigen" refers to a class of tumor antigens which arise from tumor-specific mutations in an expressed protein. The neoantigen can be derived from any cancer, tumor or cell thereof. The term encompasses both a neoantigenic peptide and a polynucleotide encoding a neoantigenic peptide. Thus, while the term "neoantigenic peptide" refers specifically to the peptide neoantigen, the term "neoantigen" more broadly encompasses the polynucleotide that encodes a neoantigenic peptide.

As used herein, the term "derived from" encompasses, without limitation: an neoantigen that is isolated or obtained directly from an originating source (e.g. a subject); a synthetic or recombinantly generated neoantigen that is identical in sequence to a neoantigen from an originating source; or a neoantigen which is made from a neoantigen of an originating source or a fragment thereof.

The mutations in the expressed protein that create the neoantigen may be patient-specific. By "patient-specific", it is meant that the mutation(s) are unique to an individual subject. However, it is possible that more than one subject will share the same mutation(s). Thus, a "patient-specific" mutation may be shared by a small or large sub-population of subjects.

In certain embodiments, the size of the neoantigenic peptide may be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino acid residues, and any range derivable therein. In some embodiments, the neoantigenic peptide is greater than 25 amino acids in length. In some embodiments, the neoantigenic peptide is 5 to 50 amino acids in length. In some embodiments, the neoantigenic peptide is 27 amino acids in length.

The neoantigenic peptide may comprise one or more neoepitopes. As used herein, the term "epitope" refers to a peptide sequence which can be recognized by the immune system, specifically by antibodies, B cells or T cells. A "neoepitope" is an epitope of a neoantigenic peptide which comprises a tumor-specific mutation as compared to the native amino acid sequence. Generally, neoepitopes may be identified by screening neoantigens for anchor residues that have the potential to bind patient HLA. The neoepitopes are normally ranked using algorithms, such as NetMHC, that can predict peptide binding to HLA.

A "T-cell neoepitope" is to be understood as meaning a mutated peptide sequence which can be bound by the MHC molecules of class I or II in the form of a peptide-presenting MHC molecule or MHC complex. The T-cell neoepitope should typically be one that is amenable to recognition by T cell receptors so that a cell-mediated immune response can occur. T-cell epitopes presented by MHC class I molecules are typically peptides between 8 and 15 amino acids in length, and more often between 9 and 11 amino acids in length. T-cell epitopes presented by MHC class II molecules are typically peptides between 5 and 24 amino acids in length, and more often between 13 and 17 amino acids in length. If the neoantigen is larger than these sizes, it will be processed by the immune system into fragments of a size more suitable for interaction with MHC class I or II molecules. Therefore, T-cell neoepitopes may be part of a larger peptide than those mentioned above.

A "B-cell neoepitope" is to be understood as meaning a mutated peptide sequence which can be recognized by B cells and/or by antibodies. B-cell epitopes are typically at least five amino acids, more often at least six amino acids, still more often at least seven or eight amino acids in length, and may be continuous ("linear") or discontinuous ("conformational"); the latter being formed, for example, by the folding of a protein to bring non-contiguous parts of the primary amino acid sequence into physical proximity. Linear B-cell epitopes typically vary from 5 to 20 amino acids in length.

In some embodiments, at least one of the neoepitopes of the neoantigenic peptide is a patient-specific neoepitope. As used herein, by "patient-specific neoepitope", it is meant that the mutation(s) in the neoepitope are unique to an individual subject. However, it is possible that more than one subject will share the same mutation(s). Thus, a "patient-specific neoepitope" may be shared by a small or large sub-population of subjects.

In an embodiment, the vaccine composition comprises at least one, at least two, at least three, at least four, at least five, or any greater number of different neoantigens. In some embodiments, the vaccine composition comprises one, two, three, four or five different neoantigens. By "different neoantigens", it is broadly meant that the neoantigens do not share the exact same sequence. The neoantigenic peptide may be from a different protein, a different tumor-specific antigen, including an over-lapping but non-identical tumor-specific antigen, or a different mutation of the same antigen. In an embodiment, each different neoantigen comprises at least one patient-specific neoepitope from the same patient.

In an embodiment, the vaccine composition comprises only one neoantigen (i.e. a single neoantigen sequence). The vaccine composition may contain multiple copies of that same neoantigen.

As is apparent from the above, neoantigenic peptides can comprise a diverse set of peptides that are unique to an individual. These peptides may have different solubility properties which would make them difficult to formulate in conventional types of vaccine formulations, such as aqueous buffer or emulsion type formulations. Additionally, there may be pre-existing tolerance to these peptides in the host from which they were derived. These aspects, among others, may cause the neoantigenic peptides to be weakly immunogenic. Therefore, it is important to deliver them in a vaccine formulation that is capable of generating a robust immune response, as disclosed herein.

In some embodiments, the vaccine compositions as disclosed herein comprise neoantigens that are weakly immunogenic. The neoantigens may be weakly immunogenic for a variety of reasons, such as lack of heterogeneity in their sequence; small size; insufficient foreignness for recognition by the immune system; decreased susceptibility to antigen processing and presentation, increased degradability or insolubility, and limited neoantigen processing and presentation due to their expression only by tumor cells. Generally, neoantigens are more susceptible to these factors than are regular antigens.

As used herein, by "weakly immunogenic" it is meant that in conventional vaccines (e.g. aqueous vaccines, emulsions, etc.), the neoantigens have little or no ability to induce, maintain and/or boost a neoantigen-specific immune response. In an embodiment, a weakly immunogenic neoantigen is one that has little or no ability to induce, maintain and/or boost a neoantigen-specific immune response after a single administration of the neoantigen.

For example, in an embodiment, a weakly immunogenic neoantigen is one that when formulated in an aqueous vaccine, is unable to sufficiently induce an immune response. In a more particular embodiment, a weakly immunogenic neoantigen is one that when formulated in an aqueous vaccine, is unable to sufficiently induce an immune response after a single administration of the vaccine composition. These embodiments are in contrast to when the same neoantigen is formulated in a comparable vaccine composition as disclosed herein (i.e. having the same components, except formulated in a hydrophobic carrier with an amphipathic compound), whereby the neoantigen is now able to sufficiently induce an immune response. In the preceding context, "sufficiently induce an immune response" means that the neoantigen is able to induce an immune response to the extent that it can provide a therapeutic effect, e.g. in the treatment of cancer.

In an embodiment, a weakly immunogenic neoantigen is one that upon exposure to the subject in an aqueous vaccine, induces no immune response or induces an immune response that is at least 2-fold, 3-fold, 4-fold, 5-fold, 6-fold, 7-fold, 8-fold, 9-fold, 10-fold, 15-fold, 20-fold, 30-fold, 40-fold or 50-fold less efficacious as compared to the immune response induced upon exposure to the subject in a vaccine composition as described herein. In an embodiment, the immune response is measured after a single administration of the neoantigen. The immune response may be measured, for example, by enzyme-linked immunospot assay (ELISPOT).

In an embodiment, a weakly immunogenic neoantigen is one that when administered in an aqueous vaccine is unable to provide a measurable therapeutic benefit to the subject; whereas a measurable therapeutic benefit can be achieved when the neoantigen is administered in a composition as disclosed herein. In an embodiment, the measureable therapeutic benefit may, for example, be a reduction in tumor size or an increased cancer survival prognosis. In an embodiment, the measurable therapeutic benefit is a reduction in tumor size of at least 25%, 50%, 75%, 80%, 85%, 90%, 95% or 100%. In an embodiment, the measurable therapeutic benefit may be detectable with a vaccine of the invention after only a single administration.

In an embodiment, a weakly immunogenic neoantigen is one that, when administered in an aqueous vaccine at a high dose amount, is less efficacious in generating an immune response than when administered at a low dose amount in a composition of the present invention. In an embodiment, the high dose amount (as measured in mice) is at least 100 micrograms, 200 micrograms, 300 micrograms, 400 micrograms, 500 micrograms or more. In an embodiment, the low dose amount (as measured in mice) is about 10 micrograms, 20 micrograms, 30 micrograms, 40 micrograms, 50 micrograms, 60 micrograms or 75 micrograms or less. The skilled person will readily appreciate equivalent or appropriate doses in humans. In an embodiment, the low dose amount is about 75%, about 70%, about 65%, about 60%, about 55%, about 50%, about 45%, about 40%, about 35%, about 30% or about 25% of the high dose amount. In an embodiment, the immune response is measured after a single administration of the neoantigen.

Without limitation, weakly immunogenic neoantigens may include, for example, purified and synthetic peptide neoantigens derived from cancer-associated antigens.

It has been postulated that weak antigenicity is a root cause of why the immune system typically fails to control tumor growth. Many cancer antigens stimulate a weak, and thus slow, immune response that provides the opportunity and time for tumor cells to develop immune evasion mechanisms and to ultimately gain the upper hand. In some embodiments, neoantigens may also exhibit this weak antigenicity.

For these reasons, among others, weakly immunogenic neoantigens may represent a particularly suitable type of neoantigen for use in the compositions and methods disclosed herein. In embodiment, the vaccine compositions disclosed herein comprise a tumor-specific neoantigen that is weakly immunogenic.

A neoantigenic peptide used to practice the invention can be isolated from natural sources, be synthetic, or be a recombinantly generated polypeptide. Neoantigenic peptides can be recombinantly expressed in vitro or in vivo. The neoantigenic peptides used to practice the invention can be made and isolated using any method known in the art. Neoantigenic peptides used to practice the invention can also be synthesized, whole or in part, using chemical methods well known in the art. See e.g., Caruthers 1980; Horn 1980; and Banga 1995. For example, peptide synthesis can be performed using various solid-phase techniques (see e.g., Roberge 1995; Merrifield 1997); and automated synthesis may be achieved, e.g., using the ABI 431A Peptide Synthesizer (Perkin Elmer) in accordance with the instructions provided by the manufacturer.

In an embodiment, the neoantigen may be selected from mutated somatic proteins of a cancer using selection algorithms such as NetMHC which look for motifs predicted to bind to MHC class I and/or MHC class II proteins (see e.g. Example 1).

In an embodiment, the neoantigen may be derived from a mutated gene or protein that has previously been associated with cancer phenotypes, such as for example tumor suppressor genes (e.g. p53); DNA repair pathway proteins (e.g. BRCA2) and oncogenes. Exemplary embodiments of genes which often contain mutations giving rise to cancer phenotypes are described, for example, in Castle 2012. The skilled person will be well aware of other mutated genes and/or proteins associated with cancer, and these are available from other literature sources.

In some embodiments, the neoantigen may comprise or consist of the neoantigens disclosed by Castle 2012. Castle 2012 does not provide the actual sequences of the neoantigens, but does provide the gene ID and location of the mutated peptide from which the actual sequence can be identified using e.g the Pubmed database available online from the National Center for Biotechnology Information (NCBI).

In an embodiment, the neoantigen may be one or more of the Mut1-50 neoantigens disclosed in Table 1 of Castle 2012, or a neoantigen of the same or related protein (e.g. a human homologue). In a particular embodiment, the neoantigen may be Mut30 having the amino acid sequence PSKPSFQEFVDWENVSPELNSTDQPFL (SEQ ID NO: 2), or a neoantigen of the same or related protein (e.g. a human homologue). Mut30 represents a neoantigen of the Kif18b gene that was identified from somatic point mutations in B16F10 murine melanoma cells. As reported by Castle 2012, KIF18B (kinesin family member 18B) is a kinesin with microtubule motor activity and ATP and nucleotide binding that is involved in the regulation of cell division. The neoantigen has a K739N mutation. Mut30 was found by Castle 2012 to induce a strong immune reaction preferentially against the mutated peptide when administered in an aqueous formulation.

As mentioned above, the term "neoantigen" also includes a polynucleotide that encodes a neoantigenic peptide. Nucleic acid-based vaccination strategies are known, wherein a vaccine composition that contains a polynucleotide is administered to a subject. The neoantigenic peptide encoded by the polynucleotide is expressed in the subject, such that the neoantigenic peptide is ultimately present in the subject, just as if the vaccine composition itself had contained the neoantigenic peptide. For the purposes of the present disclosure, the term "neoantigen", where the context dictates, encompasses such polynucleotides that encode the neoantigenic peptide which functions as the neoantigen.

The term "polynucleotide" encompasses a chain of nucleotides of any length (e.g. 9, 12, 18, 24, 30, 60, 150, 300, 600, 1500 or more nucleotides) or number of strands (e.g. single-stranded or double-stranded). Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

The polynucleotide may be delivered in various forms. In some embodiments, a naked polynucleotide may be used, either in linear form, or inserted into a plasmid, such as an expression plasmid. In other embodiments, a live vector such as a viral or bacterial vector may be used.

One or more regulatory sequences that aid in transcription of DNA into RNA and/or translation of RNA into a polypeptide may be present. In some instances, such as in the case of a polynucleotide that is a messenger RNA (mRNA) molecule, regulatory sequences relating to the transcription process (e.g. a promoter) are not required, and protein expression may be effected in the absence of a promoter. The skilled artisan can include suitable regulatory sequences as the circumstances require.

In some embodiments, the polynucleotide is present in an expression cassette, in which it is operably linked to regulatory sequences that will permit the polynucleotide to be expressed in the subject to which the composition of the invention is administered. The choice of expression cassette depends on the subject to which the composition is administered as well as the features desired for the expressed polypeptide.

Typically, an expression cassette includes a promoter that is functional in the subject and can be constitutive or inducible; a ribosome binding site; a start codon (ATG) if necessary; the polynucleotide encoding the neoantigenic peptide; a stop codon; and optionally a 3' terminal region (translation and/or transcription terminator). Additional sequences such as a region encoding a signal peptide may be included. The polynucleotide encoding the neoantigenic peptide may be homologous or heterologous to any of the other regulatory sequences in the expression cassette. Sequences to be expressed together with the neoantigenic peptide, such as a signal peptide encoding region, are typically located adjacent to the polynucleotide encoding the protein to be expressed and placed in proper reading frame. The open reading frame constituted by the polynucleotide encoding the neoantigenic peptide to be expressed solely or together with any other sequence to be expressed (e.g. the signal peptide), is placed under the control of the promoter so that transcription and translation occur in the subject to which the composition is administered.

In some embodiments, the neoantigen may be a purified neoantigen, e.g., from about 25% to 50% pure, from about 50% to about 75% pure, from about 75% to about 85% pure, from about 85% to about 90% pure, from about 90% to about 95% pure, from about 95% to about 98% pure, from about 98% to about 99% pure, or greater than 99% pure.

The amount of neoantigen used in a single treatment with a composition as described herein may vary depending on the type of neoantigen and characteristics of the subject (e.g. size, weight, age, sex, etc). One skilled in the art will be able to determine, without undue experimentation, the effective amount of neoantigen to use in a particular application. The term "effective amount" as used herein means an amount effective, at dosages and for periods of time necessary, to achieve the desired result.

In an embodiment, the amount of neoantigen used in a single dose of a composition as described herein may be from 0.001 to 5 mg/unit dose of the composition. In certain embodiments, the amount of neoantigen will be about 0.250 mg/unit dose of the composition. In certain embodiments, the amount of neoantigen will be about 1 mg/mL of the composition.

In some embodiments, the amount of neoantigen used in a single dose of a composition as described herein may be about 100 micrograms.

In some embodiments, the amount of neoantigen used in a single dose of a composition as described herein may be about 50 micrograms.

As disclosed herein, it has been surprisingly found that the oil-based compositions of the invention are capable of generating comparable immune responses against a neoantigenic peptide at both a low dose amount (e.g. 50 micrograms) and a high dose amount (e.g. 100 micrograms), after a single administration.

In an embodiment, the compositions of the invention are for delivery of a low dose amount of a neoantigen. As used herein, the term "low dose amount" refers to a lower dose amount of the neoantigen in a composition of the invention that remains capable of providing a comparable immune response to a higher dose amount of the same neoantigen in a composition of the invention and/or in a conventional type of vaccine formulation, such as an aqueous buffer or emulsion type formulation.

In an embodiment, the term "low dose amount" encompasses any dose amount of the neoantigen that is less than the minimum required dose amount to generate an immune response using an aqueous-based formulation, but is sufficient to induce an immune response using a composition of the invention.

In an embodiment, the low dose amount is about 10 micrograms, 20 micrograms, 30 micrograms, 40 micrograms, 50 micrograms, 60 micrograms or 75 micrograms or less, as measured in mice. In an embodiment, the low dose amount is about 75%, about 70%, about 65%, about 60%, about 55%, about 50%, about 45%, about 40%, about 35%, about 30% or about 25% of a high dose amount. The high dose amount may be a dose amount typically used in an aqueous-based formulation. In an embodiment, the high dose amount of the neoantigen is at least 100 micrograms, 200 micrograms, 300 micrograms, 400 micrograms, 500 micrograms or more, as measured in mice. The skilled person will readily appreciate equivalent or appropriate doses in humans based on the dosing in mice.

Amphipathic Compound

An "amphipathic compound" is a compound having both hydrophilic and hydrophobic (lipophilic) parts or characteristics. The term "amphipathic compound" may be used interchangeably with "amphiphile" or "amphiphilic". In some embodiments, suitable amphipathic compounds may also include emulsifiers such as those described herein below. Exemplary embodiments of emulsifiers that are encompassed herein by the term "amphipathic compound" include, without limitation, polysorbates (e.g. sorbitan monooleate), mannide oleate (Arlacel™ A), lecithin, Tween™ 80, and Spans™ 20, 80, 83 and 85. The amphipathic compound can facilitate the incorporation of vaccine components with hydrophilic affinity into a hydrophobic carrier such as an oil in the absence of water. The vaccine components can include, without limitation, neoantigens and/or adjuvants and/or other ingredients (e.g. T-helper epitopes) that can facilitate the production of an immune response.

Without limitation, the hydrophobic portion of an amphipathic compound is typically a large hydrocarbon moiety, such as a long chain of the form $CH_3(CH_2)_n$, with n>4. The hydrophilic portion of an amphipathic compound is usually either a charged group or a polar uncharged group. Charged groups include anionic and cationic groups. Examples of anionic charged groups include the following (wherein the hydrophobic part of the molecule is represented by "R"): carboxylates: $RCO_2^-$; sulfates: $RSO_4^-$; sulfonates: $RSO_3^-$; and phosphates (the charged functionality in phospholipids). Cationic charged groups include e.g. amines: $RNH3^+$ ("R" again representing the hydrophobic part of the molecule). Uncharged polar groups include e.g. alcohols with large R groups, such as diacyl glycerol (DAG). Amphipathic compounds may have several hydrophobic parts, several hydrophilic parts, or several of both. Proteins and some block copolymers are examples. Steroids, cholesterol, fatty acids, bile acids, and saponins, are also amphiphiles.

There are numerous amphipathic compounds which may be used, and the vaccine compositions disclosed herein may contain a single type of amphipathic compound or a mixture of different types of amphipathic compounds.

In an embodiment, the amphipathic compound is a lipid. Although any amphiphilic lipid may be used, particularly suitable lipids may include those with at least one fatty acid chain containing at least 4 carbons, and typically about 4 to 28 carbons in length. The fatty acid chain may contain any number of saturated and/or unsaturated bonds. The lipid may be a natural lipid or a synthetic lipid. Non-limiting examples of amphiphilic lipids may include phospholipids, sphingolipids, sphingomyelin, cerobrocides, gangliosides, ether lipids, sterols, cardiolipin, cationic lipids and lipids modified with poly (ethylene glycol) and other polymers. Synthetic lipids may include, without limitation, the following fatty acid constituents: lauroyl, myristoyl, palmitoyl, stearoyl, arachidoyl, oleoyl, linoleoyl, erucoyl, or combinations of these fatty acids.

In an embodiment, the amphipathic compound is a phospholipid or a mixture of phospholipids. Broadly defined, a "phospholipid" is a member of a group of lipid compounds that yield on hydrolysis phosphoric acid, an alcohol, fatty acid, and nitrogenous base.

Phospholipids that may be used include for example, and without limitation, those with at least one head group selected from the group consisting of phosphoglycerol, phosphoethanolamine, phosphoserine, phosphocholine (e.g. DOPC; 1,2-Dioleoyl-sn-glycero-3-phosphocholine) and phosphoinositol. In some embodiments, a mixture of DOPC and unesterified cholesterol may be used. In other embodiments, a mixture of Lipoid S100 lecithin and unesterified cholesterol may be used. When unesterified cholesterol is used, the cholesterol may be used in an amount equivalent to about 10% of the weight of phospholipid (e.g. in a DOPC:cholesterol ratio of 10:1 w/w or a S100 lecitin:cholesterol ratio of 10:1 w/w). The cholesterol is used to stabilize the formation of phospholipid vesicles. If a compound other than cholesterol is used, one skilled in the art can readily determine the amount needed.

In some embodiments, the compositions disclosed herein may comprise about 120 milligrams of DOPC and about 12 milligrams of cholesterol.

Another common phospholipid is sphingomyelin. Sphingomyelin contains sphingosine, an amino alcohol with a long unsaturated hydrocarbon chain. A fatty acyl side chain is linked to the amino group of sphingosine by an amide bond, to form ceramide. The hydroxyl group of sphingosine is esterified to phosphocholine. Like phosphoglycerides, sphingomyelin is amphipathic.

Lecithin, which also may be used, is a natural mixture of phospholipids typically derived from chicken eggs or sheep's wool.

All of these and other phospholipids may be used in the practice of the invention. Phospholipids can be purchased, for example, from Avanti lipids (Alabastar, Ala., USA), and lipoid LLC (Newark, N.J., USA).

In an embodiment, the amphipathic compound may be substantially evenly dispersed in the hydrophobic carrier, whereby the presence of the amphipathic compound alone is sufficient to facilitate the incorporation of vaccine components with hydrophilic affinity (e.g. a neoantigen) into a hydrophobic carrier.

In another embodiment, the amphipathic compound may be closely associated with the neoantigen so as to make the neoantigen miscible in the hydrophobic carrier. By "closely associated", it is meant that the amphipathic compound is in such proximity with the neoantigen that the neoantigen is presented in a form that it is miscible in the hydrophobic carrier. The close association may or may not involve physical interaction between the neoantigen and the amphiphile. Typically, the hydrophilic part of the amphipathic compound is oriented towards the hydrophilic moieties on the neoantigen. The amphipathic compounds may remain substantially separate from one another or they may form various different types of structures, assemblies or arrays.

Exemplary embodiments of the types of structures, assemblies or arrays that the amphipathic compounds may form include, without limitation: single layer sheets, bilayer sheets, multilayer sheets, single layer vesicular structures (e.g. micelles), bilayer vesicular structures (e.g. unilamellar or multilamellar vesicles), or various combinations thereof. By "single layer" it is meant that the amphipathic compounds do not form a bilayer, but rather remain in a layer with the hydrophobic part oriented on one side and the hydrophilic part oriented on the opposition side. By "bilayer" it is meant that the amphipathic compounds form a two-layered sheet, typically with the hydrophobic part of each layer internally oriented toward the center of the bilayer with the hydrophilic part externally oriented. However, the opposite configuration is also possible. The term "multilayer" is meant to encompass any combination of single and bilayer structures. The form adopted may depend upon the specific neoantigen, the specific amphipathic compound, and/or the specific hydrophobic carrier that is used.

In an embodiment, the structure, assembly or array formed by the amphipathic compound may partially or completely surround the neoantigen. As an example, the amphipathic compound may form a closed vesicular structure around the neoantigen.

In an embodiment, the vesicular structure is a single layer vesicular structure. An example of such a structure is a micelle. A typical micelle in aqueous solution forms an aggregate with the hydrophilic parts in contact with the surrounding aqueous solution, sequestering the hydrophobic parts in the micelle center. In contrast, in a hydrophobic carrier, an inverse/reverse micelle forms with the hydrophobic parts in contact with the surrounding aqueous solution, sequestering the hydrophilic parts in the micelle center. A spherical reverse micelle can package a neoantigen with hydrophilic affinity within its core.

In an embodiment, the vesicular structure is a micelle or an inverse/reverse micelle. Without limitation, the size of the micelles or inverse/reverse micelles range from 2 nm (20 A) to 20 nm (200 A) in diameter. In a particular embodiment, the size of the micelles or inverse/reverse micelles is about 10 nm in diameter.

In another embodiment, the vesicular structure is a bilayer vesicular structure, such as for example, a liposome. Liposomes are completely closed lipid bilayer membranes containing an entrapped aqueous volume. Liposomes may be unilamellar vesicles (possessing a single bilayer membrane) or multilamellar vesicles characterized by multimembrane bilayers, each bilayer may or may not be separated from the next by an aqueous layer. A general discussion of liposomes can be found in Gregoriadis 1990; and Frezard 1999. Liposomes can adsorb to virtually any type of cell and then release an incorporated agent (e.g. neoantigen). Alternatively, the liposome can fuse with the target cell, whereby the contents of the liposome empty into the target cell. Alternatively, a liposome may be endocytosed by cells that are phagocytic.

Liposomes have been used in the preparation of compositions comprising a hydrophobic carrier as a vesicle to encapsulate antigens as well as an emulsifier to stabilize the formulation (see e.g. WO2002/038175, WO2007/041832, WO2009/039628, WO2009/146523 and WO2013/049941). Hydrophilic antigens are typically entrapped in the aqueous interior, while hydrophobic antigens can be intercalated in the lipid bilayer or dispersed in the oil phase. In another embodiment, pre-manufactured liposomes may be used in the vaccine compositions disclosed herein.

In embodiments where the composition is water-free, one or more of the components of the composition (e.g. neoantigen, adjuvant, and/or T-helper epitope) may be encapsulated in, or mixed or suspended with, liposomes in an aqueous phase; lyophilized; and then reconstituted in the hydrophobic carrier. In such embodiments, the liposomes may reorganize to form alternate structures in the hydrophobic carrier.

Other embodiments of bilayer and mutilayer vesicular structures include, without limitation: niosomes, transfersomes, virosomes, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). The skilled artisan will recognize that the techniques for preparing these vesicular structures are well known in the art (see e.g. Kreuter 1994).

Hydrophobic Carrier

The compositions disclosed herein comprise a hydrophobic carrier, preferably a liquid hydrophobic substance. These compositions may be referred to herein interchangeably as an "oil-based formulation", an "oil-based vaccine", an "oil-based depot vaccine", an "oil-based depot forming vaccine", a "hydrophobic vaccine", a "hydrophobic composition" or a "hydrophobic vaccine composition".

The hydrophobic carrier may be an essentially pure hydrophobic substance or a mixture of hydrophobic substances. Hydrophobic substances that are useful in the compositions described herein are those that are pharmaceutically and/or immunologically acceptable. The carrier is typically a liquid but certain hydrophobic substances that are not liquids at atmospheric temperature may be liquefied, for example by warming, and may also be useful.

Oil or a mixture of oils is a particularly suitable carrier for use in the compositions disclosed herein. Oils should be pharmaceutically and/or immunologically acceptable. Suitable oils include, for example, mineral oils (especially light or low viscosity mineral oil such as Drakeol® 6VR), vegetable oils (e.g., soybean oil), nut oils (e.g., peanut oil), or mixtures thereof. Thus, in an embodiment the hydrophobic carrier is a hydrophobic substance such as vegetable oil, nut oil or mineral oil. Animal fats and artificial hydrophobic polymeric materials, particularly those that are liquid at atmospheric temperature or that can be liquefied relatively easily, may also be used.

In some embodiments, the hydrophobic carrier may be, or comprise, Incomplete Freund's Adjuvant (IFA), a mineral oil-based model hydrophobic carrier. In another embodiment, the hydrophobic carrier may be, or comprise, a mannide oleate in mineral oil solution, such as that commercially available as Montanide® ISA 51 (SEPPIC, France). While these carriers are commonly used to prepare water-in-oil emulsions, the present disclosure avoids this type of formulation by use of an amphipathic compound to suspend the components in the absence of substantial quantities of water, as described herein.

Immunovaccine Inc. has developed vaccine delivery platforms referred to as VacciMax® and DepoVax™ (DPX) (see e.g. U.S. Pat. Nos. 6,793,923 and 7,824,686; WO2002/038175; WO2007/041832; WO2009/039628; WO2009/043165 and WO2009/146523). DPX is a lipid-in-oil formulation that can be formulated with any antigen, or mixture of antigens. Unlike water-in-oil emulsion based vaccines, which rely on oil entrapping water droplets containing antigen and adjuvant, DepoVax™ based formulations rely on lipids to facilitate the incorporation of antigens and adjuvants directly into the oil, without the need for emulsification. Advantages of this approach include: (1) enhancing the solubility of hydrophilic antigens/adjuvant in oil diluents which otherwise would normally have maximum solubility in aqueous based diluents, and (2) the elimination of cumbersome emulsification procedures prior to vaccine administration.

In some embodiments, the vaccine compositions disclosed herein may comprise Immunovaccine Inc.'s delivery platform DepoVax™.

Other Components

The compositions disclosed herein may further comprise one or more additional components as are known in the art (see e.g. Remington's Pharmaceutical Sciences, Mack Publishing Company, Easton, Pa., USA 1985; and The United States Pharmacopoeia: The National Formulary (USP 24 NF19) published in 1999).

In some embodiments, the vaccine compositions may additionally comprise an adjuvant, a T-helper epitope, an emulsifier and/or an excipient.

Adjuvants

In some embodiments, the vaccine compositions disclosed herein may comprise one or more adjuvants.

A large number of adjuvants have been described and are known to those skilled in the art. Exemplary adjuvants include, without limitation, alum, other compounds of aluminum, *Bacillus* of Calmette and Guerin (BCG), TiterMax™, Ribi™, Freund's Complete Adjuvant (FCA), CpG-containing oligodeoxynucleotides (CpG ODN), lipid A mimics or analogs, lipopeptides and polyI:C polynucleotides.

An exemplary CpG ODN is (SEQ ID NO: 3)
5'-TCCAT<u>GACGTT</u>CCT<u>GACGTT</u>-3'.

The skilled person can readily select other appropriate CpG ODNs on the basis of the target species and efficacy.

An exemplary lipopeptide includes, without limitation, Pam3Cys-SKKKK (EMC Microcollections, Germany; SEQ ID NO: 4) or variants, homologs and analogs thereof. The Pam2 family of lipopeptides has been shown to be an effective alternative to the Pam3 family of lipopeptides.

In some embodiments, the pharmaceutical or vaccine compositions may comprise a polyI:C polynucleotide as an adjuvant.

PolyI:C polynucleotides are polynucleotide molecules (either RNA or DNA or a combination of DNA and RNA) containing inosinic acid residues (I) and cytidylic acid residues (C), and which induce the production of inflammatory cytokines, such as interferon. In some embodiments, the polyI:C polynucleotide is double-stranded. In such embodiments, they are typically composed of one strand consisting entirely of cytosine-containing nucleotides and one strand consisting entirely of inosine-containing nucleotides, although other configurations are possible. For instance, each strand may contain both cytosine-containing and inosine-containing nucleotides. In some instances, either or both strand may additionally contain one or more non-cytosine or non-inosine nucleotides.

In another embodiment, the polyI:C polynucleotide may be a single-stranded molecule containing inosinic acid residues (I) and cytidylic acid residues (C). As an example, and without limitation, the single-stranded polyI:C may be a sequence of repeating dIdC. In a particular embodiment, the sequence of the single-stranded polyI:C may be a 26-mer sequence of $(IC)_{13}$, i.e. ICICICICICICICICICICICICIC (SEQ ID NO: 5). As the skilled person will appreciate, due to their nature (e.g. complementarity), it is anticipated that these single-stranded molecules of repeating dIdC would naturally form homodimers, so they are conceptually similar to polyI/polyC dimers.

It has been reported that polyI:C can be segmented every 16 residues without an effect on its interferon activating potential (Bobst 1981). Furthermore, the interferon inducing potential of a polyI:C molecule mismatched by introducing a uridine residue every 12 repeating cytidylic acid residues (Hendrix 1993), suggests that a minimal double stranded polyI:C molecule of 12 residues is sufficient to promote interferon production. Others have also suggested that regions as small as 6-12 residues, which correspond to 0.5-1 helical turn of the double stranded polynucleotide, are capable of triggering the induction process (Greene 1978). If synthetically made, polyI:C polynucleotides are typically about 20 or more residues in length (commonly 22, 24, 26, 28 or 30 residues in length). If semi-synthetically made (e.g. using an enzyme), the length of the strand may be 500, 1000 or more residues.

PolyI:C acts as a mimic of viral genomes and is particularly useful for modulating the immune system in vivo. Synthetic poly I:poly C homopolymers for example have been reported to enhance innate immunity by inducing interferon gamma non-specifically when delivered systemically in vivo by intravenous or intramuscular injection (Krown 1985, Zhu 2007). Several variants of poly inosinic and cytidylic acid polymers have been described over the years (de Clercq 1978, Bobst 1981, de Clercq 1975, Guschlbauer 1977, Fukui 1977, Johnston 1975, U.S. Pat. No. 3,906,092, Kamath 2008, Ichinohe 2007), some of which included the use of covalently modified residues, the use of ribo and deoxy-ribo inosinic and cytidylic residues, the use of homopolymers and alternating co-polymers that contain inosinic and cytidylic acid residues, and the introduction of specific residues to create mismatched polymers.

The use of double stranded polynucleotides containing inosinic and cytidylic acids has been reported for the treatment of a number of viral diseases (Kende 1987, Poast 2002, U.S. Pat. No. 6,468,558, Sarma 1969, Stephen 1977, Levy 1978), cancer (Dune 1985, Salazar 1996, Theriault 1986, Nakamura 1982, Talmadge 1985, Droller 1987), autoimmune disease like multiple sclerosis (Bever 1986), and other infectious diseases such as malaria (Awasthi 1997, Puri 1996). The efficacy of polyI:C molecules has been further enhanced in some cases by complexing the molecule with positively charged poly-lysine and carboxymethyl-cellulose, effectively protecting the polynucleotide from nuclease degradation in vivo (Stephen 1977, Levy 1985), or by complexing polyI:C with positively charged synthetic peptides (Schellack 2006).

In addition to its use as a non-specific enhancer of innate immunity, polyI:C is also useful as an adjuvant in vaccine compositions. The enhancement of innate immunity can lead to an enhanced antigen specific adaptive immunity, possibly through a mechanism that involves, at least in part, NK cells, macrophages and/or dendritic cells (Chirigos 1985, Salem 2006, Alexopoulou 2001, Trumpfheller 2008). Evidence for the use of polyI:C molecules in this context originates from various vaccine studies for controlling infectious diseases (Houston 1976, Stephen 1977, Ichinohe 2007, Sloat 2008, Agger 2006, Padalko 2004) and the prevention or treatment of cancer by a variety of vaccine modalities (Zhu 2007, Cui 2006, Salem 2005, Fujimura 2006, Llopiz 2008). These studies demonstrate that polyI:C enhances humoral responses as evident from enhanced antibody responses against specific infectious disease antigens. PolyI:C is also a potentiator of antigen-specific cellular responses (Zhu 2007, Zaks 2006, Cui 2006, Riedl 2008). The adjuvanting effects of polyI:C molecules are believed to occur, at least partially, by inducing interferon-gamma through their interaction with toll like receptors (TLR) such as TLR3, TLR4, TLR7, TLR8 and TLR9 (Alexopoulou 2001, Trumpfheller 2008, Schellack 2006, Riedl 2008), with TLR3 being particularly relevant for most polyI:C molecules. Evidence also suggests that polyI:C molecules may exert their effect, at least in part, by interacting with receptors other than TLRs, such as the RNA helicase retinoic acid induced protein I (RIG-I)/melanoma differentiation associated gene 5 (MDA5) (Alexopoulou 2001, Yoneyama 2004, Gowen 2007, Dong 2008). The mechanism of action of polyI:C molecules remains to be fully understood.

Accordingly, as used herein, a "polyI:C", "polyI:C polynucleotide" or "polyI:C polynucleotide adjuvant" is a double- or single-stranded polynucleotide molecule (RNA or DNA or a combination of DNA and RNA), each strand of which contains at least 6 contiguous inosinic or cytidylic acid residues, or 6 contiguous residues selected from inosinic acid and cytidylic acid in any order (e.g. IICIIC or ICICIC), and which is capable of inducing or enhancing the production of at least one inflammatory cytokine, such as interferon, in a mammalian subject. PolyI:C polynucleotides will typically have a length of about 8, 10, 12, 14, 16, 18, 20, 22, 24, 25, 26, 28, 30, 35, 40, 45, 50, 55, 60, 65, 70, 75, 80, 85, 90, 95, 100, 150, 200, 250, 300, 500, 1000 or more residues. Preferred polyI:C polynucleotides may have a minimum length of about 6, 8, 10, 12, 14, 16, 18, 20, 22, 24, 26, 28, or 30 nucleotides and a maximum length of about 1000, 500, 300, 200, 100, 90, 80, 70, 60, 50, 45 or 40 nucleotides.

Each strand of a double-stranded polyI:C polynucleotide may be a homopolymer of inosinic or cytidylic acid residues, or each strand may be a heteropolymer containing both inosinic and cytidylic acid residues. In either case, the polymer may be interrupted by one or more non-inosinic or non-cytidylic acid residues (e.g. uridine), provided there is at least one contiguous region of 6 I, 6 C or 6 I/C residues as described above. Typically, each strand of a polyI:C polynucleotide will contain no more than 1 non-I/C residue per 6 I/C residues, more preferably, no more than 1 non-I/C residue per every 8, 10, 12, 14, 16, 18, 20, 22, 24, 26, 28 or 30 I/C residues.

The inosinic acid or cytidylic acid (or other) residues in the polyI:C polynucleotide may be derivatized or modified as is known in the art, provided the ability of the polyI:C polynucleotide to promote the production of an inflammatory cytokine, such as interferon, is retained. Non-limiting examples of derivatives or modifications include e.g. azido modifications, fluoro modifications, or the use of thioester (or similar) linkages instead of natural phosphodiester linkages to enhance stability in vivo. The polyI:C polynucleotide may also be modified to e.g. enhance its resistance to degradation in vivo by e.g. complexing the molecule with positively charged poly-lysine and carboxymethylcellulose, or with a positively charged synthetic peptide.

In some embodiments, the polyI:C polynucleotide adjuvant is a traditional form of polyI:C with an approximate molecular weight of 989,486 Daltons, containing a mixture of varying strand lengths of polyI and polyC of several hundred base pairs (Thermo Scientific; USA).

In some embodiments, the vaccine compositions as disclosed herein may comprise an adjuvant that activates or increases the activity of TLR2. As used herein, an adjuvant which "activates" or "increases the activity" of a TLR2 includes any adjuvant, in some embodiments a lipid-based adjuvant, which acts as a TLR2 agonist. Further, activating or increasing the activity of TLR2 encompasses its activation in any monomeric, homodimeric or heterodimeric form, and particularly includes the activation of TLR2 as a heterodimer with TLR1 or TLR6 (i.e. TLR1/2 or TLR2/6). Exemplary embodiments of an adjuvant that activates or increases the activity of TLR2 include lipid-based adjuvants, such as those described in WO2013/049941.

Thus, in an embodiment, the vaccine composition as disclosed herein may comprise a lipid-based adjuvant, such as disclosed for example in WO2013/049941. In an embodiment, the lipid-based adjuvant is $PAM_2Cys$-Ser-(Lys)4 (SEQ ID NO: 4) or $PAM_3Cys$-Ser-(Lys)4 (SEQ ID NO: 4).

In another embodiment, the vaccine composition as disclosed herein may comprise a lipid A mimic or analog adjuvant, such as for example those disclosed in International Patent Application No. PCT/CA2015/051309 and the references cited therein. In a particular embodiment, the adjuvant may be JL-265 or JL-266 as disclosed in PCT/CA2015/051309.

Further examples of adjuvants that may be used include, without limitation, chemokines, colony stimulating factors, cytokines, 1018 ISS, aluminum salts, Amplivax, AS04, AS15, ABM2, Adjumer, Algammulin, AS01B, AS02 (SBASA), ASO2A, BCG, Calcitriol, Chitosan, Cholera toxin, CP-870,893, CpG, polyI:C, CyaA, DETOX (Ribi Immunochemicals), Dimethyldioctadecylammonium bromide (DDA), Dibutyl phthalate (DBP), dSLIM, Gamma inulin, GM-CSF, GMDP, Glycerol, IC30, IC31, Imiquimod, ImuFact IMP321, IS Patch, ISCOM, ISCOMATRIX, JuvImmune, LipoVac, LPS, lipid core protein, MF59, monophosphoryl lipid A and analogs or mimics thereof, Montanide® IMS1312, Montanide® based adjuvants (e.g. Montanide ISA-51, -50 and -70), OK-432, OM-174, OM-197-MP-EC, ONTAK, PepTel vector system, other palmitoyl based molecules, PLG microparticles, resiquimod, squalene, SLR172, YF-17 DBCG, QS21, QuilA, P1005, Poloxamer, Saponin, synthetic polynucleotides, Zymosan, pertussis toxin.

Accordingly, the compositions herein may comprise one or more pharmaceutically acceptable adjuvants. In some embodiments, at least one of the neoantigens may be coupled to at least one of the adjuvants.

In some embodiments, the compositions herein may comprise a polyI:C polynucleotide adjuvant, a lipid-based adjuvant, a lipid A mimic or analog, or any combination thereof. In a particular embodiment, the compositions may comprise a combination of a polyI:C polynucleotide adjuvant and a lipid-based adjuvant, such as described in the adjuvanting system disclosed in U.S. Provisional Patent Application No. 62/256,875 filed on Nov. 18, 2015.

The amount of adjuvant used depends on the type and amount of neoantigen and on the type of adjuvant. One skilled in the art can readily determine the amount of adjuvant needed in a particular application by empirical testing.

T-Helper Epitopes

In some embodiments, the compositions disclosed herein may also comprise at least one T-helper epitope or T-helper antigen.

T-helper epitopes are a sequence of amino acids (natural or non-natural amino acids) that have T-helper activity. T-helper epitopes are recognised by T-helper lymphocytes, which play an important role in establishing and maximising the capabilities of the immune system, and are involved in activating and directing other immune cells, such as for example cytotoxic T lymphocytes.

A T-helper epitope can consist of a continuous or discontinuous epitope. Hence not every amino acid of a T-helper is necessarily part of the epitope. Accordingly, T-helper epitopes, including analogs and segments of T-helper epitopes, are capable of enhancing or stimulating an immune response. Immunodominant T-helper epitopes are broadly reactive in animal and human populations with widely divergent MHC types (Celis 1988, Demotz 1989, Chong 1992). The T-helper domain of the subject peptides may have from about 10 to about 50 amino acids, and more particularly about 10 to about 30 amino acids. When multiple T-helper epitopes are present, then each T-helper epitope acts independently.

In some embodiments, the T-helper epitope may form part of a neoantigen described herein. In particular, if the neoantigen is of sufficient size, it may contain an epitope that functions as a T-helper epitope. In other embodiments, the T-helper epitope is a separate molecule from the neoantigen. In other embodiments, the T-helper epitope may be fused to the neoantigen.

In another embodiment, T-helper epitope analogs may include substitutions, deletions and insertions of from one to about 10 amino acid residues in the T-helper epitope. T-helper segments are contiguous portions of a T-helper epitope that are sufficient to enhance or stimulate an immune response. An example of T-helper segments is a series of overlapping peptides that are derived from a single longer peptide.

In a particular embodiment, the compositions as disclosed herein may comprise as a T-helper epitope or antigen, the modified Tetanus toxin peptide A16L (830 to 844; AQYIKANSKFIGITEL (SEQ ID NO: 1), with an alanine residue added to its amino terminus to enhance stability (Slingluff 2001).

Other sources of T-helper epitopes which may be used in the present compositions include, for example, hepatitis B surface antigen helper T cell epitopes, pertussis toxin helper T cell epitopes, measles virus F protein helper T cell epitope, Chlamydia trachomitis major outer membrane protein helper T cell epitope, diphtheria toxin helper T cell epitopes, Plasmodium falciparum circumsporozoite helper T cell epitopes, *Schistosoma mansoni* triose phosphate isomerase helper T cell epitopes, *Escherichia coli* TraT helper T cell epitopes and immune-enhancing analogs and segments of any of these T-helper epitopes.

In some embodiments, the T-helper epitope may be a universal T-helper epitope. A universal T-helper epitope as used herein refers to a peptide or other immunogenic molecule, or a fragment thereof, that binds to a multiplicity of MEW class II molecules in a manner that activates T cell function in a class II (CD4+ T cells)-restricted manner. An example of a universal T-helper epitope is PADRE (pan-DR epitope) comprising the peptide sequence AKXVAAWTLKAAA (SEQ ID NO: 6), wherein X may be cyclohexylalanyl. PADRE specifically has a CD4+ T-helper epitope, that is, it stimulates induction of a PADRE-specific CD4+ T-helper response.

In addition to the modified tetanus toxin peptide A16L mentioned earlier, Tetanus toxoid has other T-helper epitopes that work in the similar manner as PADRE. Tetanus and diphtheria toxins have universal epitopes for human CD4+ cells (Diethelm-Okita 2000). In another embodiment, the T-helper epitope may be a tetanus toxoid peptide such as F21E comprising the peptide sequence FNNFTVSFWLRVPKVSASHLE (amino acids 947-967; SEQ ID NO: 7).

In certain embodiments, the T-helper epitope is fused to at least one of the one or more neoantigens in the composition as disclosed herein (e.g. a fusion peptide).

Emulsifiers

In some embodiments, the vaccine compositions disclosed herein may comprise one or more emulsifiers. The emulsifier may be a pure emulsifying agent or a mixture of emulsifying agents. The emulsifier(s) should be pharmaceutically and/or immunologically acceptable.

The use of an emulsifier may be of particular relevance to preparing compositions that are water-free or substantially free of water. For instance, in some embodiments an emulsifier may be used to assist in stabilizing the amphipathic compound, mixture of amphipathic compound and neoantigen, or the mixture of amphipathic compound, neoantigen and other vaccine components (e.g. polyI:C and/or lipid-based adjuvant, T-helper epitope, etc.) when the amphipathic compound or mixtures are resuspended into the hydrophobic carrier. The use of an emulsifier may, for example, promote more even distribution of the amphipathic compound or mixture in the hydrophobic carrier.

The emulsifier may be amphipathic and therefore, the emulsifier may include a broad range of compounds. In some embodiments, the emulsifier may be a surfactant, such as for example, a non-ionic surfactant. Examples of emulsifiers which may be used include polysorbates, which are oily liquids derived from polyethylene glycolyated sorbital, and sorbitan esters. Polysorbates may include, for example, sorbitan monooleate. Typical emulsifiers are well-known in the art and include, without limitation, mannide oleate (Arlacel™ A), lecithin, Tween™ 80, Spans™ 20, 80, 83 and 85. In an embodiment, the emulsifier for use in the vaccine compositions is mannide oleate.

The emulsifier is generally pre-mixed with the hydrophobic carrier. In some embodiments, a hydrophobic carrier which already contains an emulsifier may be used. For example, a hydrophobic carrier such Montanide™ ISA 51 already contains the emulsifier mannide oleate. In other embodiments, the hydrophobic carrier may be mixed with emulsifier before combining with the amphipathic compound, mixture of amphipathic compound and neoantigen, or the mixture of amphipathic compound, neoantigen and other vaccine components (e.g. polyI:C and/or lipid-based adjuvant, T-helper epitope, etc.).

The emulsifier is used in an amount effective to promote even distribution of the amphipathic compound in the hydrophobic carrier and/or to assist in the formation of structures, assemblies or arrays described herein. Typically, the volume ratio (v/v) of hydrophobic carrier to emulsifier is in the range of about 5:1 to about 15:1, more particularly 10:1.

Water-Free Embodiments of the Compositions

In an embodiment, the vaccine compositions disclosed herein are water-free or substantially free of water, i.e. the vaccine compositions are not emulsions.

By "water-free" it is meant that the compositions contain no water at all. In another embodiment, the compositions may be substantially free of water. The term "substantially free of water" is intended to encompass embodiments where the hydrophobic carrier may still contain small quantities of water, provided that the water is present in the non-continuous phase of the carrier. For example, individual components of the composition may have small quantities of bound water that may not be completely removed by processes such as lyophilization or evaporation and certain hydrophobic carriers may contain small amounts of water dissolved therein. Generally, compositions as disclosed herein that are "substantially free of water" contain, for example, less than about 10%, 9%, 8%, 7%, 6%, 5%, 4%, 3%, 2%, 1%, 0.5%, 0.1%, 0.05% or 0.01% water on a weight/weight basis of the total weight of the carrier component of the composition. The compositions that still contain small quantities of water do not contain a sufficient amount of water such that an emulsion would be formed.

It is contemplated that water-free vaccine compositions as disclosed herein may be capable of generating significantly higher antibody titres and more potent cell-mediated immune responses with lower doses of one or more of the components, e.g. neoantigen, adjuvant(s), T-helper epitope, etc. This is based on the unique mechanism of action of DepoVax™ in forcing active uptake of the vaccine components.

Without being held to any particular theory of action, it is thought that when a water-free composition of the present disclosure is used, the formulation creates a strong depot that persists over several weeks allowing prolonged clearance of neoantigen and interaction of the vaccine with the immune system. In this regard, it has been reported that lipid-in-oil based formulations achieve peak clearance within 3 weeks of immunization, and clearance continues at a slower rate over six months (Brewer et al. 2014). This is in contrast to aqueous vaccine formulations which release antigens quickly over a few hours to a week; or emulsions which form a short-lived depot.

Kits and Reagents

The vaccine compositions disclosed herein are optionally provided to a user as a kit. For example, a kit of the present disclosure contains one or more components of the compositions disclosed herein. The kit can further comprise one or more additional reagents, packaging material, containers for holding the components of the kit, and an instruction set or user manual detailing preferred methods of using the kit components. In an embodiment, the containers are vials.

In an embodiment, the kit contains pre-formulated vaccine in separate containers in a ready-to-use format. As an example, in an embodiment, the kit comprises at least one container comprising an amphipathic compound, a neoantigen and a hydrophobic carrier. The pre-formulated vaccine in each separate container may be the same or different.

In an alternative embodiment of the kit, the vaccine may be provided with all components, except hydrophobic carrier, in one container (e.g. as a dry cake) ready for reconstitution in the hydrophobic carrier or as individual components in separate containers for formulation, lyophilization and reconstitution in the hydrophobic carrier.

In an embodiment, the kit may comprise a first container comprising an amphipathic compound and a neoantigen; and a second container comprising a hydrophobic carrier. In this embodiment, the vaccine components in the first container may be in the form of a dry cake that is ready to be re-suspended in the hydrophobic carrier.

In various aspects of the above kit embodiments, in addition to neoantigen, amphipathic compound and hydrophobic carrier, the vaccine may optionally further comprise one or more of a T-helper epitope, an adjuvant, and an emulsifier. These components may be provided individually in separate containers or may be provided as any combination thereof together in a container, such as together in a container with the neoantigen and amphipathic compound.

In an embodiment of the kit, the T-helper epitope is a peptide comprising the amino acid sequence FNNFTVSFWLRVPKVSASHLE (SEQ ID NO: 7).

In an embodiment of the kit, the T-helper epitope is a peptide comprising the amino acid sequence AQYIKANSKFIGITEL (SEQ ID NO: 1).

In an embodiment of the kit, the adjuvant is a polyI:C polynucleotide.

In an embodiment of the kit, the amphipathic compound is one or more lipids, such as phospholipids. In an embodiment, the lipids are 1,2-dioleoyl-sn-glycero-3-phosphocholine (DOPC) and cholesterol.

In an embodiment, the kit may additionally contain an agent that interferes with DNA replication. The agent that interferes with DNA replication may be included in the kit in a separate container, or the agent may be included with other components. In a particular embodiment, the agent that interferes with DNA replication that is included in the kit is an alkylating agent, such as for example, cyclophosphamide.

In an embodiment, the kit may additionally contain an immune response checkpoint inhibitor. The immune response checkpoint inhibitor may be included in the kit in a separate container, or it may be included with other components. The immune response checkpoint inhibitor may be an inhibitor of Programmed Death-Ligand 1 (PD-L1), Programmed Death 1 (PD-1), CTLA-4, PD-L2, LAG3, TIM3, 41BB, 2B4, A2aR, B7H1, B7H3, B7H4, BTLA, CD2, CD27, CD28, CD30, CD40, CD70, CD80, CD86, CD160, CD226, CD276, DR3, GALS, GITR, HVEM, IDO1, IDO2, inducible T cell costimulatory (ICOS), KIR, LAIR1, LIGHT, macrophage receptor with collageneous structure (MARCO), phosphatidylserine (PS), OX-40, SLAM, TIGIT, VISTA, VTCN1, or any combination thereof.

The skilled person will appreciate that alternate arrangements of the kit are possible and are encompassed by the disclosure herein.

The kit as disclosed herein may be used in practicing the methods disclosed herein. In an embodiment, the kit is for use in inducing an antibody immune response and/or cell-mediated immune response to the neoantigen in a subject. In an embodiment that may be particularly suitable, the kit is for preparing a vaccine composition that is water-free or substantially free of water.

Immune Responses and Methods of Use

The compositions disclosed herein may find application in any instance in which it is desired to administer a neoantigen to a subject. The subject may be a vertebrate, such as a fish, bird or mammal, preferably a human.

As referred to herein, the "immune response" may either be a cell-mediated immune response or an antibody (humoral) immune response.

In some embodiments, the vaccine compositions disclosed herein may be used for inducing a cell-mediated immune response to the neoantigen.

As used herein, to "induce" an immune response is to elicit and/or potentiate an immune response. Inducing an immune response encompasses instances where the immune response is enhanced, elevated, improved or strengthened to the benefit of the host relative to the prior immune response status, for example, before the administration of a composition disclosed herein.

As used herein, the terms "cell-mediated immune response", "cellular immunity", "cellular immune response" or "cytotoxic T-lymphocyte (CTL) immune response" (used interchangeably herein) refer to an immune response characterized by the activation of macrophages and natural killer cells, the production of neoantigen-specific cytotoxic T lymphocytes and/or the release of various cytokines in response to a neoantigen. Cytotoxic T lymphocytes are a sub-group of T lymphocytes (a type of white blood cell) which are capable of inducing the death of infected somatic or tumor cells; they kill cells that are infected with viruses (or other pathogens), or that are otherwise damaged or dysfunctional.

Most cytotoxic T cells express T cell receptors that can recognise a specific peptide antigen bound to Class I MHC molecules. Typically, cytotoxic T cells also express CD8 (i.e. CD8+ T cells), which is attracted to portions of the Class I MHC molecule. This affinity keeps the cytotoxic T cell and the target cell bound closely together during antigen-specific activation.

Cellular immunity protects the body by, for example, activating antigen-specific cytotoxic T-lymphocytes (e.g. antigen-specific CD8+ T cells) that are able to lyse body cells displaying epitopes of foreign or mutated antigen on their surface, such as cancer cells displaying tumor-specific neoantigens; activating macrophages and natural killer cells, enabling them to destroy intracellular pathogens; and stimulating cells to secrete a variety of cytokines that influence the function of other cells involved in adaptive immune responses and innate immune responses.

Cellular immunity is an important component of the adaptive immune response and following recognition of neoantigen by cells through their interaction with neoantigen-presenting cells such as dendritic cells, B lymphocytes and to a lesser extent, macrophages, protect the body by various mechanisms such as:

1. activating antigen-specific cytotoxic T-lymphocytes that are able to induce apoptosis in body cells displaying epitopes of foreign or mutated antigen on their surface, such as cancer cells displaying tumor-specific neoantigens;

2. activating macrophages and natural killer cells, enabling them to destroy intracellular pathogens; and 3. stimulating cells to secrete a variety of cytokines that influence the function of other cells involved in adaptive immune responses and innate immune responses.

Cell-mediated immunity is most effective in removing virus-infected cells, but also participates in defending against fungi, protozoans, cancers, and intracellular bacteria. It also plays a major role in transplant rejection.

Since cell-mediated immunity involves the participation of various cell types and is mediated by different mechanisms, several methods could be used to demonstrate the induction of immunity following vaccination. These could be broadly classified into detection of: i) specific antigen presenting cells; ii) specific effector cells and their functions and iii) release of soluble mediators such as cytokines.

i) Antigen presenting cells: Dendritic cells and B cells (and to a lesser extent macrophages) are equipped with special immunostimulatory receptors that allow for enhanced activation of T cells, and are termed professional antigen presenting cells (APC). These immunostimulatory molecules (also called co-stimulatory molecules) are up-regulated on these cells following infection or vaccination, during the process of antigen presentation to effector cells such as CD4 and CD8 cytotoxic T cells. Such co-stimulatory molecules (such as CD40, CD80, CD86, MHC class I or MHC class II) can be detected, for example, by using flow cytometry with fluorochrome-conjugated antibodies directed against these molecules along with antibodies that specifically identify APC (such as CD11c for dendritic cells).

ii) Cytotoxic T cells: (also known as Tc, killer T cell, or cytotoxic T-lymphocyte (CTL)) are a sub-group of T cells which induce the death of cells that are infected with viruses (and other pathogens), or expressing tumor antigens or neoantigens. These CTLs directly attack other cells carrying certain foreign or abnormal molecules on their surface. The ability of such cellular cytotoxicity can be detected using in vitro cytolytic assays (chromium release assay). Thus, induction of adaptive cellular immunity can be demonstrated by the presence of such cytotoxic T cells, wherein, when neoantigen loaded target cells are lysed by specific CTLs that are generated in vivo following vaccination or infection.

Naive cytotoxic T cells are activated when their T cell receptor (TCR) strongly interacts with a peptide-bound MHC class I molecule. This affinity depends on the type and orientation of the antigen/MHC complex, and is what keeps the CTL and infected cell bound together. Once activated the CTL undergoes a process called clonal expansion in which it gains functionality, and divides rapidly, to produce an army of "armed"-effector cells. Activated CTL will then travel throughout the body in search of cells bearing that unique MHC Class I+peptide. This could be used to identify such CTLs in vitro by using peptide-MHC Class I tetramers in flow cytometric assays.

When exposed to these infected or dysfunctional somatic cells, effector CTL release perform and granulysin: cytotoxins which form pores in the target cell's plasma membrane, allowing ions and water to flow into the infected cell, and causing it to burst or lyse. CTL release granzyme, a serine protease that enters cells via pores to induce apoptosis (cell death). Release of these molecules from CTL can be used as a measure of successful induction of cell-mediated immune response following vaccination. This can be done by enzyme linked immunosorbant assay (ELISA) or enzyme linked immunospot assay (ELISPOT) where CTLs can be quantitatively measured. Since CTLs are also capable of producing important cytokines such as IFN-γ, quantitative measurement of IFN-γ-producing CD8 cells can be achieved by ELISPOT and by flowcytometric measurement of intracellular IFN-γ in these cells.

CD4+ "helper" T cells: CD4+ lymphocytes, or helper T cells, are immune response mediators, and play an important role in establishing and maximizing the capabilities of the adaptive immune response. These cells have no cytotoxic or phagocytic activity; and cannot kill infected cells or clear pathogens, but, in essence "manage" the immune response, by directing other cells to perform these tasks. Two types of effector CD4+ T helper cell responses can be induced by a professional APC, designated Th1 and Th2, each designed to eliminate different types of pathogens.

Helper T cells express T cell receptors (TCR) that recognize antigen bound to Class II MHC molecules. The activation of a naive helper T cell causes it to release cytokines, which influences the activity of many cell types, including the APC that activated it. Helper T cells require a much milder activation stimulus than cytotoxic T cells. Helper T cells can provide extra signals that "help" activate cytotoxic cells. Two types of effector CD4+ T helper cell responses can be induced by a professional APC, designated Th1 and Th2, each designed to eliminate different types of pathogens. The two Th cell populations differ in the pattern of the effector proteins (cytokines) produced. In general, Th1 cells assist the cell-mediated immune response by activation of macrophages and cytotoxic T cells; whereas Th2 cells promote the humoral immune response by stimulation of B cells for conversion into plasma cells and by formation of antibodies. For example, a response regulated by Th1 cells may induce IgG2a and IgG2b in mouse (IgG1 and IgG3 in humans) and favor a cell mediated immune response to a neoantigen. If the IgG response to an antigen is regulated by Th2 type cells, it may predominantly enhance the production of IgGI in mouse (IgG2 in humans). The measure of cytokines associated with Th1 or Th2 responses will give a measure of successful vaccination. This can be achieved by specific ELISA designed for Th1-cytokines such as IFN-γ, IL-2, IL-12, TNF-α and others, or Th2-cytokines such as IL-4, IL-5, IL10 among others.

iii) Measurement of cytokines: released from regional lymph nodes gives a good indication of successful immunization. As a result of neoantigen presentation and maturation of APC and immune effector cells such as CD4 and CD8 T cells, several cytokines are released by lymph node cells. By culturing these LNC in vitro in the presence of neoantigen, a neoantigen-specific immune response can be detected by measuring release if certain important cytokines such as IFN-γ, IL-2, IL-12, TNF-α and GM-CSF. This could be done by ELISA using culture supernatants and recombinant cytokines as standards.

Successful immunization may be determined in a number of ways known to the skilled person including, but not limited to, hemagglutination inhibition (HAIJ) and serum neutralization inhibition assays to detect functional antibodies; challenge studies, in which vaccinated subjects are challenged with the associated pathogen to determine the efficacy of the vaccination; and the use of fluorescence activated cell sorting (FACS) to determine the population of cells that express a specific cell surface marker, e.g. in the identification of activated or memory lymphocytes. A skilled person may also determine if immunization with a composition as disclosed herein elicited an antibody and/or cell mediated immune response using other known methods. See, for example, Coligan et al., ed. Current Protocols in Immunology, Wiley Interscience, 2007.

In an embodiment, the composition disclosed herein is capable of generating an enhanced cell-mediated immune response that is at least 2-fold, at least 3-fold, at least 4-fold, at least 5-fold, at least 6-fold, at least 7-fold, at least 8-fold, at least 9-fold or at least 10-fold greater than when the neoantigen is formulated in an aqueous-based vaccine formulation. By "aqueous-based vaccine", it is meant a vaccine that comprises identical components as the oil-based formulations described herein, with the exception that the hydrophobic carrier is replaced with an aqueous carrier and the aqueous-based vaccine does not comprise an amphipathic compound.

In an embodiment, the composition disclosed herein is capable of generating the enhanced cell-mediated immune response with only a single administration of the composition. Thus, in an embodiment, the compositions disclosed herein are for delivery of the neoantigen by single administration.

In an embodiment, the composition disclosed herein is capable of generating the enhanced cell-mediated immune response by a low dose amount of the neoantigen, wherein the low dose amount is about 50% of the dose amount in the aqueous-based vaccine formulation.

In some embodiments, the vaccine compositions disclosed herein may be used for inducing an antibody immune response to the neoantigen.

An "antibody immune response" or "humoral immune response" (used interchangeably herein), as opposed to cell-mediated immunity, is mediated by secreted antibodies which are produced in the cells of the B lymphocyte lineage (B cells). Such secreted antibodies bind to antigens, such as for example those on the surfaces of foreign substances, pathogens (e.g. viruses, bacteria, etc.) and/or cancer cells, and flag them for destruction.

As used herein, "humoral immune response" refers to antibody production and may also include, in addition or alternatively, the accessory processes that accompany it, such as for example the generation and/or activation of T-helper 2 (Th2) or T-helper 17 (Th17) cells, cytokine production, isotype switching, affinity maturation and memory cell activation. "Humoral immune response" may also include the effector functions of an antibody, such as for example toxin neutralization, classical complement activation, and promotion of phagocytosis and pathogen elimination. The humoral immune response is often aided by CD4+ Th2 cells and therefore the activation or generation of this cell type may also be indicative of a humoral immune response. The term "humoral immune response" is used interchangeably herein with "antibody response" or "antibody immune response".

An "antibody" is a protein comprising one or more polypeptides substantially or partially encoded by immunoglobulin genes or fragments of immunoglobulin genes. The recognized immunoglobulin genes include the κ, λ, α, γ, δ, ε and μ constant region genes, as well as myriad immunoglobulin variable region genes. Light chains are classified as either κ c or λ. Heavy chains are classified as γ, μ, α, δ, or ε, which in turn define the immunoglobulin classes, IgG, IgM, IgA, IgD and IgE, respectively. A typical immunoglobulin (antibody) structural unit comprises a protein containing four polypeptides. Each antibody structural unit is composed of two identical pairs of polypeptide chains, each having one "light" and one "heavy" chain. The N-terminus of each chain defines a variable region primarily responsible for antigen recognition. Antibody structural units (e.g. of the IgA and IgM classes) may also assemble into oligomeric forms with each other and additional polypeptide chains, for example as IgM pentamers in association with the J-chain polypeptide.

Antibodies are the antigen-specific glycoprotein products of a subset of white blood cells called B lymphocytes (B cells). Engagement of neoantigen with antibody expressed on the surface of B cells can induce an antibody response comprising stimulation of B cells to become activated, to undergo mitosis and to terminally differentiate into plasma cells, which are specialized for synthesis and secretion of antigen-specific antibody.

B cells are the sole producers of antibodies during an immune response and are thus a key element to effective humoral immunity. In addition to producing large amounts of antibodies, B cells also act as antigen-presenting cells and can present neoantigenic peptide to T cells, such as T helper CD4 or cytotoxic CD8+ T cells, thus propagating the immune response. B cells, as well as T cells, are part of the adaptive immune response. During an active immune response, induced for example by either vaccination or natural infection, antigen-specific B cells are activated and clonally expand. During expansion, B cells evolve to have higher affinity for the epitope. Proliferation of B cells can be induced indirectly by activated T-helper cells, and also directly through stimulation of receptors, such as the TLRs.

Antigen presenting cells, such as dendritic cells and B cells, are drawn to vaccination sites and can interact with neoantigens and adjuvants contained in a vaccine composition. Typically, the adjuvant stimulates the cells to become activated and the neoantigen provides the blueprint for the target. Different types of adjuvants may provide different stimulation signals to cells. For example, polyI:C (a TLR3 agonist) can activate dendritic cells, but not B cells. Adjuvants such as Pam3Cys, Pam2Cys and FSL-1 are especially adept at activating and initiating proliferation of B cells, which is expected to facilitate the production of an antibody response (Moyle 2008; So 2012).

A humoral immune response is one of the common mechanisms for effective infectious disease vaccines (e.g. to protect against viral or bacterial invaders). However, a humoral immune response can also be useful for combating cancer. Whereas a cancer vaccine is typically designed to produce a cell-mediated immune response that can recognize and destroy cancer cells, B cell mediated responses may target cancer cells through other mechanisms which may in some instances cooperate with a cytotoxic T cell for maximum benefit. Examples of B cell mediated (e.g. humoral immune response mediated) anti-tumor responses include, without limitation: 1) Antibodies produced by B cells that bind to surface antigens (e.g. neoantigens) found on tumor cells or other cells that influence tumorigenesis. Such antibodies can, for example, induce killing of target cells through antibody-dependant cell-mediated cytotoxicity (ADCC) or complement fixation, potentially resulting in the release of additional antigens that can be recognized by the immune system; 2) Antibodies that bind to receptors on tumor cells to block their stimulation and in effect neutralize their effects; 3) Antibodies that bind to factors released by or associated with a tumor or tumor-associated cells to modulate a signaling or cellular pathway that supports cancer; and 4) Antibodies that bind to intracellular targets and mediate anti-tumor activity through a currently unknown mechanism.

One method of evaluating an antibody response is to measure the titers of antibodies reactive with a particular antigen. This may be performed using a variety of methods known in the art such as enzyme-linked immunosorbent assay (ELISA) of antibody-containing substances obtained from animals. For example, the titers of serum antibodies which bind to a particular neoantigen may be determined in a subject both before and after exposure to the neoantigen. A statistically significant increase in the titer of neoantigen-specific antibodies following exposure to the neoantigen would indicate the subject had mounted an antibody response to the neoantigen.

Without limitation, other assays that may be used to detect the presence of an neoantigen-specific antibody include immunological assays (e.g. radioimmunoassay (RIA)), immunoprecipitation assays, and protein blot (e.g. Western blot) assays; and neutralization assays (e.g., neutralization of viral infectivity in an in vitro or in vivo assay).

The vaccine compositions disclosed herein may be useful for treating or preventing diseases and/or disorders ameliorated by a cell-mediated immune response or a humoral immune response. The vaccines may find application in any instance in which it is desired to administer a neoantigen to a subject to induce a cell-mediated immune response or a humoral immune response. In an embodiment, the vaccines may find application for the delivery of a personalized vaccine.

In an embodiment, the present disclosure relates to a method comprising administering the composition as described herein to a subject in need thereof. In some embodiments, the method is for inducing an antibody immune response and/or cell-mediated immune response to a neoantigen in said subject. In some embodiments, the method is for the treatment and/or prevention of cancer.

"Treating" or "treatment of", or "preventing" or "prevention of", as used herein, refers to an approach for obtaining beneficial or desired results. Beneficial or desired results can include, but are not limited to, alleviation or amelioration of one or more symptoms or conditions, diminishment of extent of disease, stabilisation of the state of disease, prevention of development of disease, prevention of spread of disease, delay or slowing of disease progression (e.g. suppression), delay or slowing of disease onset, conferring protective immunity against a disease-causing agent and amelioration or palliation of the disease state. "Treating" or "preventing" can also mean prolonging survival of a patient beyond that expected in the absence of treatment and can also mean inhibiting the progression of disease temporarily or preventing the occurrence of disease, such as by preventing infection in a subject. "Treating" or "preventing" may also refer to a reduction in the size of a tumor mass, reduction in tumor aggressiveness, etc.

In an embodiment, the methods and compositions disclosed herein may be for use in treating and/or preventing cancer in a subject in need thereof. The subject may have cancer or may be at risk of developing cancer.

As used herein, the terms "cancer", "cancer cells", "tumor" and "tumor cells", (used interchangeably) refer to cells that exhibit abnormal growth, characterized by a significant loss of control of cell proliferation or cells that have been immortalized. The term "cancer" or "tumor" includes metastatic as well as non-metastatic cancer or tumors. A cancer may be diagnosed using criteria generally accepted in the art, including the presence of a malignant tumor.

Without limitation, cancers that may be capable of being treated and/or prevented by the use or administration of a composition as disclosed herein include carcinoma, adenocarcinoma, lymphoma, leukemia, sarcoma, blastoma, myeloma, and germ cell tumors. Without limitation, particularly suitable embodiments may include glioblastoma, multiple myeloma, ovarian cancer, breast cancer, fallopian tube cancer, prostate cancer or peritoneal cancer. In one embodiment, the cancer may be caused by a pathogen, such as a virus. Viruses linked to the development of cancer are known to the skilled person and include, but are not limited to, human papillomaviruses (HPV), John Cunningham virus (JCV), Human herpes virus 8, Epstein Barr Virus (EBV), Merkel cell polyomavirus, Hepatitis C Virus and Human T cell leukaemia virus-1 The cancer is one that expresses one or more tumor-specific neoantigens.

In a particular embodiment, the cancer is breast cancer, ovarian cancer, prostate cancer, fallopian tube cancer, peritoneal cancer, glioblastoma or diffuse large B cell lymphoma.

The methods and compositions disclosed herein may be useful for either the treatment or prophylaxis of cancer; for example, a reduction of the severity of cancer (e.g. size of the tumor, aggressiveness and/or invasiveness, malignancy, etc) or the prevention of cancer recurrences.

In an embodiment, the method for treating and/or preventing cancer first comprises identifying one or more neoantigens or neoepitopes in the patients' tumor cells. The skilled person will understand methods known in the art that can be used to identify the one or more neoantigens (see, for example, Srivastava 2015 and the references cited therein). As an exemplary embodiment, whole genome/exome sequencing may be used to identify mutated neoantigens that are uniquely present in a tumor of an individual patient. The collection of identified neoantigens can be analyzed to select (e.g. based on algorithms) a specific, optimized subset of neoantigens and/or neoepitopes for use as a personalized cancer vaccine.

Having identified and selected one or more neoantigens, one of skill in the art will appreciate that there are a variety of ways in which to produce such neoantigens either in vitro or in vivo. The neoantigenic peptides may be produced by any method known the art and then may be formulated into a vaccine composition or kit as described herein and administered to a subject.

In an embodiment, upon administration to a subject, the vaccine composition induces a tumor-specific immune response in the treatment of cancer. By this it is meant that the immune response specifically targets the tumor cells without a significant effect on normal cells of the body which do not express the neoantigen. Further, in an embodiment, the composition may comprise at least one patient-specific neoepitope such that the tumor-specific immune response is patient-specific for the subject or a subset of subjects, i.e. a personalized immunotherapy.

The vaccine composition as disclosed herein may be administered by any suitable route. In an embodiment, the route of administration is subcutaneous injection.

Agent that Interferes with DNA Replication

The methods disclosed herein may also comprise administering an agent that interferes with DNA replication. In a particular embodiment, an agent that interferes with DNA replication is administered when the methods disclosed herein are used in the treatment or prevention of cancer.

Exemplary embodiments of such agents and methods of use thereof are described, for example, in WO2014/153636.

As used herein, the expression "interferes with DNA replication" is intended to encompass any action that prevents, inhibits or delays the biological process of copying (i.e., replicating) the DNA of a cell. The skilled person will appreciate that there exist various mechanisms for preventing, inhibiting or delaying DNA replication, such as for example DNA cross-linking, methylation of DNA, base substitution, etc. The methods according to the invention encompass the use of any agent that interferes with DNA replication by any means known in the art. In an exemplary embodiment, and without limitation, the agent that interferes with DNA replication is a drug.

In an embodiment, the agent that interferes with DNA replication is one which, when used at doses that are non-chemotherapeutic, is capable of selectively affecting DNA replication in cells of the immune system, with the intent of modulating the immune system to enhance vaccine responses. By "non-chemotherapeutic", it is meant that the dose of the agent is a dose lower than that which would be used to directly and selectively destroy malignant or cancerous cells and tissues.

Other embodiments of an agent that interferes with DNA replication include agents that interfere with DNA replication to cause programmed cell death, with the ability to selectively target rapidly dividing cells of the immune system. The purpose of such agents is to modulate cells of the immune system to enhance vaccine responses. Such agents are typically used at doses that are not expected to be chemotherapeutic and are considered acceptable for use in humans. The purpose of selectively targeting immune cells may be to reduce the number of immune suppressive cells, and/or deplete useful immune cells involved in mediating the immune response for the purposes of inducing rapid proliferation upon removal of the drug targeting DNA replication.

Interference with DNA replication leading to cell death may be caused by numerous mechanisms, including but not limited to, the formation of DNA cross-linking (e.g. by alkylating agents, platinum compounds, etc.), methylation of DNA (i.e. by methylating agents), base substitution (i.e. by nucleoside analogs). Exemplary agents and their mechanisms are described in Cancer Chemotherapy and Biotherapy: Principles and Practice (Cabner B. A., $5^{th}$ edition, Lippincott Williams & Wilkins, PA, USA, 2011).

In an embodiment, the agent that interferes with DNA replication is an alkylating agent. Alkylating agents include, but are not limited to, cyclophosphamide, temozolomide, ifosfamide, mafosfamide, melphalan, busulfan, bendamustine, uramustine, carmustine or bis-chloroethylnitrosourea (BCNU), chlorambucil, mitomycin C, and their derivatives, active metabolites or metabolite intermediates. A suitable derivative may be, for example and without limitation, palifosfamide (e.g. a derivative of ifosfamide).

In another embodiment, the agent that interferes with DNA replication is a platinum compound. Platinum compounds include, but are not limited to, carboplatin, cisplatin, oxaliplatin and their derivatives.

In another embodiment, the agent that interferes with DNA replication is a methylating agent. Methylating agents include, but are not limited to, temzolomide, procarbazine and dacarbazine, and their derivatives.

In another embodiment, the agent that interferes with DNA replication is a nucleoside analog. Non-limiting examples of nucleoside analogs include gemcitabine, 5-fluorouracil, cytosine arabinoside (Ara-C) and their derivatives.

In another embodiment, any drug that inhibits DNA replication indirectly by inhibiting enzymes critical to DNA replication, such as topoisomerase I, topoisomerase II or DNA polymerase, may also be used. Such drugs include, for example and without limitation, doxorubicin, daunorubicin, mitoxantrone, etoposide, teniposide, topotecan, camptothecin, irinotecan, acyclovir and ganciclovir.

Exemplary agents that interfere with DNA replication, and which may be used in the methods of the invention include, without limitation, those listed below in Table 1. As the skilled person will appreciate, these are examples of agents that may be used. Additional agents include, for example, any drug or compound that interferes with DNA replication by a similar mechanism and/or that has a similar functional group.

TABLE 1

| DNA Replication Inhibitor | Functional group | Description | Exemplary Agents |
| --- | --- | --- | --- |
| Alkylating agents | Nitrogen mustard (bischloroethylamine) $RN(CH_2CH_2Cl)_2$ | Alkylate DNA | Cyclophosphamide Ifosfamide Mafosfamide Melphalan Bendamustine Uramustine Palifosfamide Chlorambucil 4-Hydroxycyclophosphamide |

TABLE 1-continued

| DNA Replication Inhibitor | Functional group | Description | Exemplary Agents |
|---|---|---|---|
| Alkylating agents | Nitrosourea | Alkylate DNA | Bis-chloroethylnitrosourea (BCNU) |
| Alkylating agents | Alkyl sulfonates | Alkylate DNA | Busulfan |
| Antitumor Antibiotics | Aziridines or Ethylene imines | Alkylate DNA and Intercalate DNA | Mitomycin C<br><br>Yondelis |
| Methylating Agents | Reactive N-methyl group | Methylate DNA | Procarbazine<br>Dacarbazine<br>Temozolomide |

TABLE 1-continued

| DNA Replication Inhibitor | Functional group | Description | Exemplary Agents |
| --- | --- | --- | --- |
| Platinum compounds | Pt(II) | Covalently binds to DNA | Cisplatin Carboplatin Oxaliplatin |
| Nucleoside analogs | Resemble purine or pyrimidine bases | Incorporate into DNA during replication | Acyclovir Gemcitabine 5-fluorouracil Cytosine arabinoside Ganciclovir |
| Camptothecin derivatives | Quinoline alkaloids | Inhibits activity of topoisomerase I | Camptothecin Topotecan Irinotecan |
| Anthracycline derivatives | Anthracycline antibiotics | Inhibit activity of topoisomerase II | Doxorubicin Daunorubicin Epirubicin Idarubicin |
| Epipodophyllotoxin derivatives | Epipodophyllotoxin | Inhibit activity of topoisomerase II | Etoposide Teniposide |
| Anthracenedione derivatives | Anthracenedione | Intercalate DNA | Mitoxantrone Pixantrone |

In a particular embodiment, the agent that interferes with DNA replication is a nitrogen mustard alkylating agent, or any intermediary or active metabolite thereof. Nitrogen mustards are non-specific DNA alkylating agents. Nitrogen mustards form cyclic aminium ions (aziridinium rings) by intramolecular displacement of the chloride by the amine nitrogen. This azidirium group is then capable of alkylating DNA by attacking the N-7 nucleophilic center on the guanine base. Upon displacement of the second chlorine, a second alkylation step occurs that results in the formation of interstrand cross-links (ICLs). These lesions are highly cytotoxic since they block fundamental metabolic processes such as DNA replication and transcription.

The methods of the invention encompass the use of any such non-specific nitrogen mustard DNA alkylating agents. Particularly suitable nitrogen mustard alkylating agents may include for example, and without limitation, cyclophosphamide, palifosfamide, bendamustine, and ifosfamide.

Ifosfamide is a nitrogen mustard alkylating agent. The IUPAC name for ifosfamide is N-3-bis(2-chloroethyl)-1,3, 2-oxazaphosphinan-2-amide-2-oxide. Ifosfamide is commonly known as Ifex®. The chemical structure of ifosfamide is:

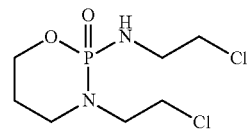

Palifosfamide is an active metabolite of ifosfamide that is covalently linked to the amino acid lysine for stability. Palifosfamide irreversibly alkylates and cross-links DNA through GC base pairs, resulting in irreparable 7-atom inter-strand cross-links; inhibition of DNA replication and/ or cell death. Palifosfamide is also known as Zymafos®.

Bendamustine is another nitrogen mustard alkylating agent. The IUPAC name for Bendamustine is 4-[5-[Bis(2- chloroethyl)amino]-1-methylbenzimidazol-2-yl]butanoic acid, and it is commonly referred to as Treakisym®, Ribomustin®, Levact® and Treanda®. The chemical structure of bendamustine is:

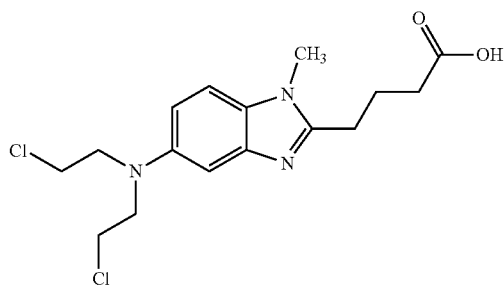 [SMILES: Cn1c(CCCC(=O)O)nc2cc(N(CCCl)CCCl)ccc21]

Also encompassed by the methods of the invention is the use of intermediary and/or active metabolites of DNA alkylating agents, and particularly intermediary and/or active metabolites of the nitrogen mustard DNA alkylating agents described herein. Such metabolites include, without limitation, aldophosphamide, 4-hydroxycyclophosphamide, 4-hydroxyifosfamide, chloracetaldehyde and phosphamide mustard.

In a further embodiment, the agent that interferes with DNA replication may be any suitable pharmaceutically acceptable salt, ester, tautomer, stereoisomer, racemic mixture, solvate, hydrate or prodrug of the alkylating agents, platinum compounds, methylating agents, or nucleoside analogs described herein.

In a particular embodiment, the agent that interferes with DNA replication for use in the methods of the invention is cyclophosphamide. Cyclophosphamide (N,N-bis(2-chloroethyl)-1,3,2-oxazaphosphinan-2-amine 2-oxide), also known as cytophosphane, is a nitrogen mustard alkylating agent. The chemical structure of cyclophosphamide is:

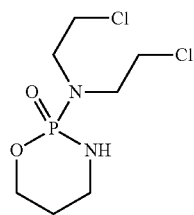 [SMILES: O=P1(N(CCCl)CCCl)NCCCO1]

Cyclophosphamide is also known and referred to under the trade-marks Endoxan®, Cytoxan®, Neosar®, Procytox® and Revimmune®. Other nitrogen mustard alkylating agents in the same class as cyclophosphamide include, without limitation, palifosfamide, bendamustine and ifosfamide.

Cyclophosphamide (CPA) is a prodrug which is typically administered via intravenous infusion, but also can be administered parenterally and orally (de Jonge 2005) with little difference in bioavailability (Juma 1979). CPA is converted to its active metabolites, 4-hydroxy-CPA and aldophosphamide, by oxidation by P450 enzymes in the liver (Emmenegger 2007, Emmenegger 2011). The active metabolites of CPA are lipid soluble and enter cells through passive diffusion. Intracellular 4-OH-CPA spontaneously decomposes into phosphoramide mustard which is the ultimate active metabolite. Phosphoramide mustard catalyzes intra- and interstrand DNA cross-links as well as DNA-protein cross-links that inhibit DNA replication leading to cell death (de Jonge 2005). Phosphoramide mustard is eliminated by enzymatic conversion to carboxyphoshphamide by cytoplasmic aldehyde dehydrogenase (ALDH) (Emmenegger 2007, Emmenegger 2011).

Cells with low levels of ALDH tend to accumulate CPA metabolites and are more sensitive to its effects, and indeed tumor upregulation of ALDH is one mechanism of CPA resistance (Zhang 2005). Besides ALDH, low intracellular ATP levels have also been associated with CPA selectivity towards particular cells types (Zhao 2010). At high doses, typically in the range of 1-5 $g/m^2$, the effects of CPA are most cytotoxic to rapidly dividing cells indiscriminate of cell type, and CPA is myelosuppressive since most hematogenic cells are rapidly dividing (Bruce 1996; Smith 1985).

Total systemic clearance of CPA and its metabolites varies between 5-9 hours, and peak plasma levels of the parent also vary considerably between patients (3-11 hours) reflecting genetic differences in metabolism from person to person (Cohen 1971; Mouridsen 1974). Repeated administration of CPA is reported to shorten elimination half-life by increasing activity of enzymes involved in metabolism (D'Incalci 1979), but whether this leads to increased metabolism of the active metabolite is not known (de Jonge, Huitema et al. 2005), particularly at low doses (Emmenegger 2007).

Dose translation from human to murine studies is calculated using the following equation:

$$\text{Human dose (mg/kg)} = \text{Animal } Km$$

$$\text{Animal dose (mg/kg)} = \text{Human } Km$$

Where the constant mouse Km value is 3 and human Km value is 37 (Reagan-Shaw, Nihal et al. 2008).

In the last two decades, low dose CPA has been appreciated for its immune modulatory and anti-angiogenic effects. In contrast to high dose CPA, low doses of CPA, typically 100-300 $mg/m^2$, lack widespread cytotoxic activity but do appear to enhance immune-mediated tumor elimination by selectively modulating cells of the immune system and also by reducing angiogenesis within the tumor microenvironment. The mechanisms of action and uses of low dose CPA are further described, for example, in WO2014/153636.

In an embodiment, the methods disclosed herein comprise administering an agent that interferes with DNA replication.

The agent that interferes with DNA replication is typically administered in an amount sufficient to provide an immune-modulating effect. As used herein, the expression "immune-modulating effect" refers to the ability of the agent that interferes with DNA replication to alter (modulate) one or more aspects of the immune system and/or cells of the immune system. In an embodiment, the "amount sufficient to provide an immune-modulating effect" is an amount of the agent that is capable of selectively affecting DNA replication in cells the immune system. For example, the amount of agent may be an amount sufficient to selectively target rapidly dividing cells of the immune system to cause programmed cell death.

The "amount sufficient to provide an immune-modulating effect" may interchangeably be referred to herein as a "low dose" amount. As relates to a particular embodiment of the invention where the agent that interferes with DNA replication is the alkylating agent cyclophosphamide, the expression "low dose" typically refers to a dose of cyclophosphamide that is less than or equal to 300 mg/m$^2$, such as for example 25-300 mg/m$^2$ and more particularly 100-300 mg/m$^2$. In an embodiment, the low dose amount of cyclophosphamide is 10, 25, 50, 75 or 100 mg BID (two times daily). In a particular embodiment, the low dose amount of cyclophosphamide is 50 mg BID. The "low dose" amounts of other agents that interfere with DNA replication, as encompassed herein, would be known to those skilled in the art, or could be determined by routine skill.

In a particular embodiment, the methods disclosed herein comprise a cycle of low dose metronomic cyclophosphamide. For purposes of the present disclosure, "metronomic" is meant to refer to a frequent administration of a lower than normal dose amount of the agent that interferes with DNA replication (e.g. cyclophosphamide). As used herein, the term "normal dose amount" may refer, for example and without limitation, to either: (i) the established maximum tolerated dose (MTD) or standard dose via a traditional dosing schedule, or (ii) in instances where a low dose single bolus amount has been established for a particular agent that interferes with DNA replication, than to that low dose amount.

In metronomic dosing, the same, lower, or higher cumulative dose over a certain time period as would be administered via a traditional dosing schedule may ultimately be administered. In a particularly suitable embodiment, this is achieved by extending the time frame during which the dosing is conducted and/or increasing the frequency of administrations, while decreasing the amount administered as compared to the normal dose amount. For example, where a low dose amount of 300 mg/m$^2$ of an agent that interferes with DNA replication is typically administered (e.g. by single bolus injection), a metronomic regimen may comprise administering the same amount over a period of several days by administering frequent low doses.

In an embodiment of the methods disclosed herein, metronomic treatment with the agent that interferes with DNA replication (e.g. cyclophosphamide) is intended to encompass a daily low dose administration of the agent over a certain period of time, such as for example a period of 2, 3, 4, 5, 6 or 7, or more, consecutive days. During these days of metronomic dosing, the agent that interferes with DNA replication may be provided at frequent regular intervals or varying intervals. For example, in an embodiment, a dose of the agent that interferes with DNA replication may be administered every 1, 2, 3, 4, 6, 8, 12 or 24 hours. In another embodiment, a dose of the agent that interferes with DNA replication may be administered once every 2, 3, or 4 days. In a particular embodiment, a dose of the agent that interferes with DNA replication may be administered two times daily.

In some embodiments, there may be breaks or gaps in the periods of metronomic treatment with the agent that interferes with DNA replication. In this manner, metronomic treatment may occur in a cyclic fashion, alternating between on and off periods of administration. Particularly suitable are intervals where the agent that interferes with DNA replication is administered to the subject daily on alternating weekly intervals. For instance, a one week period of administration of the agent that interferes with DNA replication is followed by a one week suspension of treatment, and the cycle repeats.

In an embodiment therefore, the methods disclosed herein comprise administering the agent that interferes with DNA replication to the subject daily for a period of 7 consecutive days, beginning every second week. In a particular aspect of this embodiment, the administration of the agent that interferes with DNA replication begins about 7 days prior to the first administration of the depot-forming vaccine. In a further aspect of this embodiment, the agent that interferes with DNA replication may be administered at a dose of 50 mg BID (two times daily) on each day of administration.

In an embodiment of the methods disclosed herein, the agent that interferes with DNA replication may be administered as a priming agent during the intermittent period between each administration of the depot-forming vaccine and/or non-depot-forming vaccine.

As the skilled person will appreciate, the frequency and duration of the administration of the agent that interferes with DNA replication, as well as the administration of the depot-forming and non-depot-forming vaccines, may be adjusted as desired for any given subject within the parameters described above. Factors that may be taken into account include, e.g.: the nature of the one or more neoantigens in the vaccine; the type of disease or disorder; the age, physical condition, body weight, sex and diet of the subject; and other factors.

The agent that interferes with DNA replication may be administered by any suitable delivery means and any suitable route of administration. In an embodiment, the agent that interferes with DNA replication is administered orally, such as in the form of a pill, tablet or capsule. In an alternate embodiment, the agent is administered by injection (e.g. intravenous). In a particular embodiment of the methods disclosed herein, the agent is cyclophosphamide and it is administered orally.

In a particular embodiment of the methods disclosed herein, the agent that interferes with DNA replication is cyclophosphamide.

Checkpoint Inhibitor

The methods disclosed herein may also comprise administering an immune response checkpoint inhibitor.

As used herein, an "immune response checkpoint inhibitor" refers to any compound or molecule that totally or partially reduces, inhibits, interferes with or modulates one or more checkpoint proteins. Checkpoint proteins regulate T-cell activation or function. Numerous checkpoint proteins are known, such as for example CTLA-4 and its ligands CD80 and CD86; and PD-1 and its ligands PD-L1 and PD-L2. Checkpoint proteins are responsible for co-stimulatory or inhibitory interactions of T-cell responses. Checkpoint proteins regulate and maintain self-tolerance and the duration and amplitude of physiological immune responses. Herein, the term "immune response checkpoint inhibitor" may be used interchangeably with "checkpoint inhibitor".

In some embodiments, the immune response checkpoint inhibitor is an inhibitor of Programmed Death-Ligand 1 (PD-L1, also known as B7-H1, CD274), Programmed Death 1 (PD-1, CD279), CTLA-4 (CD154), PD-L2 (B7-DC, CD273), LAG3 (CD223), TIM3 (HAVCR2, CD366), 41BB (CD137), 2B4, A2aR, B7H1, B7H3, B7H4, BTLA, CD2, CD27, CD28, CD30, CD40, CD70, CD80, CD86, CD160, CD226, CD276, DR3, GALS, GITR, HVEM, IDO1, IDO2, ICOS (inducible T cell costimulator), KIR, LAIR1, LIGHT, MARCO (macrophage receptor with collageneous structure), PS (phosphatidylserine), OX-40, SLAM, TIGIT, VISTA, VTCN1, or any combination thereof.

In some embodiments, the immune response checkpoint inhibitor is an inhibitor of PD-L1, PD-1, CTLA-4 or any combination thereof.

In some embodiments, the immune response checkpoint inhibitor is an inhibitor of PD-L1 or PD-1. In an embodiment, the inhibitor of PD-L1 or PD-1 may be an anti-PD-1 or anti-PD-L1 antibody, such as for example and without limitation, those disclosed in WO 2015/103602. For example, in an embodiment, the anti-PD-1 antibody or anti-PD-L1 antibody may be selected from: nivolumab, pembrolizumab, pidilizumab, BMS-936559 (see ClinicalTrials.gov; Identifier NCT02028403), MPDL3280A (Roche, see ClinicalTrials.gov; Identifier NCT02008227), MDX1105-01 (Bristol Myers Squibb, see ClinicalTrials.gov; Identifier NCT00729664), MEDI4736 (MedImmune, see ClinicalTrials.gov; Identifier NCT01693562), and MK-3475 (Merck, see ClinicalTrials.gov; Identifier NCT02129556). In an embodiment, the anti-PD-1 antibody may be RMP1-4 or J43 (BioXCell) or a human or humanized counterpart thereof.

In some embodiments, the immune response checkpoint inhibitor is an inhibitor of CTLA-4. In an embodiment, the inhibitor of CTLA-4 may be an antibody, such as for example and without limitation, ipilimumab (Bristol-Myers Squibb) or BN13 (BioXCell). In another embodiment, the anti-CTLA-4 antibody may be UC10-4F10-11, 9D9 or 9H10 (BioXCell) or a human or humanized counterpart thereof.

The one or more immune response checkpoint inhibitors may be administered by any suitable route. In some embodiments, the route of administration of the one or more immune response checkpoint inhibitors is parenteral, mucosal, oral, sublingual, transdermal, topical, inhalation, intranasal, aerosol, intraperitoneal, intratumoral, intraocular, intratracheal, intrarectal, intragastric, vaginal, by gene gun, dermal patch or in eye drop or mouthwash form. In an embodiment, the immune response checkpoint inhibitor may be administered by subcutaneous injection.

As the skilled person will appreciate, the frequency and duration of the administration of the immune response checkpoint inhibitor may be adjusted as desired for any given subject. Factors that may be taken into account include, e.g.: the nature and type of the specific checkpoint inhibitor; the nature of the one or more neoantigens in the vaccine; the type of disease or disorder; the age, physical condition, body weight, sex and diet of the subject; and other factors.

In some embodiments, the one or more immune response checkpoint inhibitors may be administered before, after or concurrently with the depot-forming vaccine and/or non-depot-forming vaccine. In an embodiment, the immune response checkpoint inhibitor may be administered at a time subsequent to the first administration with the depot-forming vaccine. In aspects of this embodiment, the immune response checkpoint inhibitor may be administered at a time before or after the first administration of the non-depot-forming vaccine.

In an embodiment, administration of the immune response checkpoint inhibitor may begin on the same day as the first administration of the depot-forming vaccine and may be administered at a desired schedule thereafter. In an embodiment, the desired schedule may be administration of the immune response checkpoint inhibitor every 1, 2, 3, 4, 6, 8, 12 or 18 hours; every 1, 2, 3, 4, 5 or 6 days; or every 1, 2, 3 or 4 weeks. In an embodiment, the desired schedule may be once every 3 days.

There may be breaks or gaps in the periods of administration of the immune response checkpoint inhibitor. In this manner, administration may occur in a cyclic fashion, alternating between on and off periods of administration.

Methods for Preparing the Vaccine Compositions

The vaccine compositions may be prepared by known methods in the art having regard to the present disclosure. Exemplary embodiments for preparing the vaccine compositions disclosed herein are described below, without limitation.

As used in this section, the term "neoantigen" is used generally to describe how a neoantigen may be formulated in the vaccine compositions of the present disclosure. The term "neoantigen" encompasses both the singular form "neoantigen" and the plural "neoantigens". It is not necessary that all neoantigens be introduced into the vaccine composition in the same way.

In an embodiment for preparing the vaccine composition, the neoantigen and optionally other vaccine components (e.g. adjuvant, T-helper epitope, etc.) are reconstituted in a suitable solvent together with an amphipathic compound. The vaccine components are then dried to form a dry cake, and the dry cake is resuspended in a hydrophobic carrier. The step of drying may be performed by various means known in the art, such as by freeze-drying, lyophilization, rotary evaporation, evaporation under pressure, etc. Low heat drying that does not compromise the integrity of the components can also be used. Heat can also be used to assist in resuspending the neoantigen/amphipathic compound mixture.

The "suitable solvent" is one that is suitable for solubilizing the neoantigen, adjuvants and/or amphipathic compound, and can be determined by the skilled person. In an embodiment, sodium phosphate buffer (0.2M, pH 6.0) or sodium phosphate buffer (0.1M, pH 7.0) may be used. In an embodiment, acetate buffer (0.1M, pH 9.5) may be used. In another embodiment, a polar protic solvent such as an alcohol (e.g. tert-butanol, n-butanol, isopropanol, n-propanol, ethanol or methanol), water, acetate buffer, formic acid or chloroform may be used. In some cases, the same solvent can be used to solubilize each of the amphipathic compound, neoantigen and adjuvants, and the solubilized components are then mixed. Alternatively, the neoantigen, adjuvants and amphipathic compound may be mixed prior to solubilization, and then solubilized together. In a further alternative, only one or more of the amphipathic compound, neoantigen or adjuvants are solubilized, and the non-solubilized component(s) are added.

In a particular embodiment, to prepare the vaccine compositions the neoantigen and adjuvants are reconstituted together or separately in sodium phosphate buffer with S100 lipids and cholesterol (Lipoid, Germany). These vaccine components are then lyophilized to form a dry cake. Just prior to injection, the dry cake is resuspended in ISA51 VG oil (SEPPIC, France) to prepare a water-free oil-based vaccine composition.

In a particular embodiment, to prepare the vaccine compositions the neoantigen and adjuvants are reconstituted together or separately in acetate buffer (0.1M, pH 9.5) with DOPC and cholesterol (Lipoid, Germany). These vaccine components are then lyophilized to form a dry cake. Just prior to injection, the dry cake is resuspended in ISA51 VG oil (SEPPIC, France) to prepare a water-free oil-based vaccine composition.

In another embodiment, to prepare the vaccine compositions a conjugated neoantigen/T-helper epitope is reconstituted in 0.2% PEG-$H_2O$ with lipids DOPC and cholesterol (Lipoid, Germany). The polyI:C and lipid-based adjuvants are reconstituted in water, and then added to the neoantigen-lipid mixture. These vaccine components are then lyophilized to form a dry cake. Just prior to injection, the dry cake is resuspended in ISA51 VG oil (SEPPIC, France) to prepare a water-free vaccine composition.

In the above embodiments, without being bound to a particular theory of action, it is believed that removal (drying) of the solvent leaves the vaccine components, including the neoantigen, in an array of amphipathic compound molecules with their hydrophilic head groups oriented towards the vaccine components. The vaccine components and amphipathic compound can then be suspended in the hydrophobic carrier (such as oil) in the absence of water, since they have been made sufficiently hydrophobic.

Additional components as described herein, such as T-helper epitope, may be added at any stage in the formulation process. For instance, one or more such additional components may be combined with the neoantigen, adjuvants and/or amphipathic compound either before or after solubilization, or added to the solubilized mixture. In another embodiment, the additional components may instead be added to or combined with the dried mixture of neoantigen, adjuvants and amphipathic compound, or combined with the hydrophobic carrier either before or after resuspension of the dry mixture of neoantigen, adjuvants and amphipathic compound in the hydrophobic carrier. In an embodiment, the T-helper epitope is added to the vaccine composition in the same way as the neoantigen. In an embodiment, the neoantigen and T-helper epitope are a fused peptide.

In some embodiments, it may be appropriate to include an emulsifier in the hydrophobic carrier to assist in stabilizing the vaccine components of the dry cake when they are resuspended in the hydrophobic carrier. The emulsifier is provided in an amount sufficient to resuspend the dry mixture of neoantigen, adjuvants and amphipathic compound in the hydrophobic carrier and maintain the neoantigen, adjuvants and amphipathic compound in suspension in the hydrophobic carrier. For example, the emulsifier may be present at about 5% to about 15% weight/weight or weight/volume of the hydrophobic carrier.

Stabilizers such as sugars, anti-oxidants, or preservatives that maintain the biological activity or improve chemical stability to prolong the shelf life of any of the vaccine components, may be added to such compositions.

EMBODIMENTS (1) A vaccine composition comprising:
(a) an amphipathic compound;
(b) a neoantigen; and
(c) a hydrophobic carrier.

(2) The composition of paragraph (1), wherein the composition is water-free or substantially free of water.

(3) The composition of paragraph (2), wherein a composition that is substantially free of water comprises less than about 10%, 9%, 8%, 7%, 6%, 5%, 4%, 3%, 2%, 1%, 0.5%, 0.1%, 0.05% or 0.01% water on a weight/weight basis of the total weight of the carrier.

(4) The composition of any one of paragraphs (1) to (3), wherein the neoantigen is a neoantigenic peptide or a polynucleotide encoding a neoantigenic peptide.

(5) The composition of paragraph (4), wherein the neoantigenic peptide is 5 to 50 amino acids in length.

(6) The composition of paragraph (4) or (5), wherein the neoantigenic peptide comprises one or more neoepitopes.

(7) The composition of paragraph (6), wherein the one or more neoepitopes are selected from: an MHC class I T-cell neoepitope of 9 to 11 amino acids in length; an MHC class II T-cell neoepitope of 13 to 17 amino acids in length; or a B-cell neoepitope of 5 to 20 amino acids in length.

(8) The composition of any one of paragraphs (1) to (7), wherein the neoantigen comprises the amino acid sequence PSKPSFQEFVDWENVSPELNSTDQPFL (SEQ ID NO: 2).

(9) The composition of paragraph (6) or (7), wherein at least one of the one or more neoepitopes is a patient-specific neoepitope.

(10) The composition of any one of paragraphs (1) to (9), which comprises one, two, three, four or five different neoantigens, optionally wherein each different neoantigen is derived from a different tumor-specific antigen.

(11) The composition of paragraph (10), wherein each different neoantigen comprises at least one patient-specific neoepitope from the same patient.

(12) The composition of any one of paragraphs (1) to (11), wherein the neoantigen is a weakly immunogenic antigen.

(13) The composition of any one of paragraphs (1) to (12), wherein the composition comprises a low dose amount of the neoantigen.

(14) The composition of any one of paragraphs (1) to (13), wherein the neoantigen is sufficiently hydrophobic, or is made sufficiently hydrophobic, such that the neoantigen is miscible in the hydrophobic carrier.

(15) The composition of paragraph (14), wherein the neoantigen is made sufficiently hydrophobic by the presence of the amphipathic compound.

(16) The composition of paragraph (15), wherein the amphipathic compound is closely associated with the neoantigen to make the neoantigen miscible in the hydrophobic carrier.

(17) The composition of paragraph (16), wherein the amphipathic compound forms a sheet or vesicular structure, partially or completely surrounding the neoantigen.

(18) The composition of any one of paragraphs (1) to (17), wherein the amphipathic compound is a lipid, for example a phospholipid or a mixture of phospholipids; optionally selected from dioleoyl phosphatidylcholine (DOPC), lecithin (e.g. Lipoid S100), or a mixture thereof.

(19) The composition of paragraph (18), wherein the lipids form a closed vesicular structure around the neoantigen, for example a single layer vesicular structure (e.g. a micelle) or a bilayer vesicular structure (e.g. a unilamellar or multilamellar liposome).

(20) The composition of any one of paragraphs (1) to (19), wherein the hydrophobic carrier is an oil or a mixture of oils, optionally selected from a vegetable oil, nut oil, mineral oil, or a mixture thereof.

(21) The composition of paragraph (20), wherein the hydrophobic carrier is mineral oil or is a mannide oleate in mineral oil solution, for example Montanide® ISA 51.

(22) The composition of any one of paragraphs (1) to (21) further comprising an adjuvant.

(23) The composition of paragraph (22), wherein the adjuvant is a polyI:C polynucleotide adjuvant, a lipid-based adjuvant, a lipid A mimic or analog, or any combination thereof.

(24) The composition of paragraph (23), wherein the lipid-based adjuvant is PAM$_2$Cys-Ser-(Lys)4 (SEQ ID NO: 4) or PAM$_3$Cys-Ser-(Lys)4 (SEQ ID NO: 4).

(25) The composition of any one of paragraphs (1) to (24) further comprising a T-helper epitope.

(26) The composition of paragraph (25), wherein the T-helper epitope is PADRE comprising the amino acid sequence AKXVAAWTLKAAA (SEQ ID NO: 6); Tetanus toxoid peptide F21E comprising the amino acid sequence FNNFTVSFWLRVPKVSASHLE (SEQ ID NO: 7); or modified Tetanus toxin peptide A16L comprising the amino acid sequence AQYIKANSKFIGITEL (SEQ ID NO: 1).

(27) The composition of paragraph (26), wherein the T-helper epitope is optionally conjugated or fused to the neoantigen.

(28) The composition of any one of paragraphs (1) to (27), which comprises:

(a) a lipid molecule mixture of 1,2-dioleoyl-sn-glycero-3-phosphocholine (DOPC) and cholesterol;

(b) a neoantigen;

(c) the hydrophobic carrier Montanide® ISA 51;

(d) a universal T-helper epitope from tetanus toxoid comprising the amino acid sequence AQYIKANSKFIGITEL (SEQ ID NO: 1); and (e) a polyI:C polynucleotide adjuvant.

(29) The composition of any one of paragraphs (1) to (28) for use in inducing an antibody immune response and/or a cell-mediated immune response to the neoantigen in a subject.

(30) The composition of any one of paragraphs (1) to (29), which generates an enhanced cell-mediated immune response that is at least 2-fold, at least 3-fold, at least 4-fold, at least 5-fold, at least 6-fold, at least 7-fold, at least 8-fold, at least 9-fold or at least 10-fold greater than when the neoantigen is formulated in an aqueous-based vaccine formulation.

(31) The composition of paragraph 20, wherein the enhanced cell-mediated immune response is:

provided by only a single immunization with the composition; and/or provided by a low dose amount of the neoantigen in the composition, wherein the low dose amount is about 50% of the dose amount in the aqueous-based vaccine formulation.

(32) A method comprising administering the composition of any one of paragraphs (1) to (31) to a subject in need thereof.

(33) The method according to paragraph (32), which is a method for inducing an antibody immune response and/or a cell-mediated immune response to the neoantigen in the subject.

(34) The method of paragraph (33) which comprises only a single administration of the composition to the subject.

(35) The method of paragraph (33) or (34), wherein the composition comprises a low dose amount of the neoantigen.

(36) The method according to any one of paragraphs (33) to (35), which is a method for the treatment and/or prevention of cancer.

(37) The method according to paragraph (36), wherein the composition induces a tumor-specific immune response in the treatment of the cancer.

(38) The method according to paragraph (37), wherein the composition comprises at least one patient-specific neoepitope and the tumor-specific immune response is patient-specific for the subject.

(39) The method according to any one of paragraphs (32) to (38), which further comprises administering to the subject an agent that interferes with DNA replication.

(40) The method according to paragraph (39), wherein the agent that interferes with DNA replication is cyclophosphamide.

(41) The method according to paragraph (40), which comprises a cycle of low dose metronomic cyclophosphamide, wherein the cycle comprises administering the cyclophosphamide to the subject daily for a period of 7 consecutive days, beginning every second week.

(42) The method according to any one of paragraphs (32) to (41), which further comprises administering to the subject an immune response checkpoint inhibitor.

(43) The method according to paragraph (42), wherein the immune response checkpoint inhibitor is an inhibitor of Programmed Death-Ligand 1 (PD-L1), Programmed Death 1 (PD-1), CTLA-4, PD-L2, LAG3, TIM3, 41BB, 2B4, A2aR, B7H1, B7H3, B7H4, BTLA, CD2, CD27, CD28, CD30, CD40, CD70, CD80, CD86, CD160, CD226, CD276, DR3, GALS, GITR, HVEM, IDO1, IDO2, inducible T cell costimulatory (ICOS), KIR, LAIR1, LIGHT, macrophage receptor with collageneous structure (MARCO), phosphatidylserine (PS), OX-40, SLAM, TIGIT, VISTA, VTCN1, or any combination thereof.

(44) Use of the composition of any one of paragraphs (1) to (31) for inducing an antibody immune response and/or a cell-mediated immune response to said neoantigen in the subject.

(45) The use according to paragraph (44) which comprises only a single administration of the composition to the subject.

(46) The use according to paragraph (44) or (45), wherein the composition comprises a low dose amount of the neoantigen.

(47) The use according to any one of paragraphs (44) to (46), wherein the antibody immune response and/or the cell-mediated immune response is a tumor-specific immune response.

(48) Use of the composition of any one of paragraphs (1) to (31) for the treatment and/or prevention of cancer.

(49) The use according to paragraph (48) which comprises only a single administration of the composition to the subject.

(50) The use according to paragraph (48) or (49), wherein the composition comprises a low dose amount of the neoantigen.

(51) The use according to any one of paragraphs (44) to (50), which further comprises use of an agent that interferes with DNA replication and/or an immune response checkpoint inhibitor.

(52) The use according to paragraph (51), wherein the agent that interferes with DNA replication is cyclophosphamide.

(53) The use according to paragraph (51) or (52), wherein the immune response checkpoint inhibitor is an inhibitor of Programmed Death-Ligand 1 (PD-L1), Programmed Death 1 (PD-1), CTLA-4, PD-L2, LAG3, TIM3, 41BB, 2B4, A2aR, B7H1, B7H3, B7H4, BTLA, CD2, CD27, CD28, CD30, CD40, CD70, CD80, CD86, CD160, CD226, CD276, DR3, GALS, GITR, HVEM, IDO1, IDO2, inducible T cell costimulatory (ICOS), KIR, LAIR1, LIGHT, macrophage receptor with collageneous structure (MARCO), phosphatidylserine (PS), OX-40, SLAM, TIGIT, VISTA, VTCN1, or any combination thereof.

(54) A kit comprising: a first container comprising an amphipathic compound and a neoantigen; and a second container comprising a hydrophobic carrier.

(55) The kit of paragraph (54), wherein the amphipathic compound in the first container comprise 1,2-dioleoyl-sn-glycero-3-phosphocholine (DOPC) and cholesterol.

(56) The kit of paragraph (55) or (56), wherein the first container further comprises a T-helper epitope.

(57) The kit of paragraph (56), wherein the T-helper epitope is a peptide comprising the amino acid sequence AQYIKANSKFIGITEL (SEQ ID NO: 1).

(58) The kit of any one of paragraphs (54) to (57), wherein the first container further comprises an adjuvant.

(59) The kit of paragraph (58), wherein the adjuvant is a polyI:C polynucleotide.

(60) The kit of any one of paragraphs (54) to (59), wherein the components of the first container were subject to lyophilization to form a dry cake.

(61) The kit of any one of paragraphs (54) to (60), for use in inducing an antibody immune response and/or a cell-mediated immune response to the neoantigen in a subject.

(62) The kit of any one of paragraphs (54) to (61) which comprises a sufficient amount of the components for only a single administration.

(63) The kit of any one of paragraphs (54) to (62), wherein the kit comprises a low dose amount of the neoantigen.

The invention is further illustrated by the following non-limiting examples.

EXAMPLES

Example 1 i) Identification and Synthesis of Neoantigens

To identify neoantigens, the whole exome of a tumor is sequenced (RNA and/or genomic DNA) and screened against normal tissue genome, preferably from the same patient. This is performed using next generation sequencing. Somatic gene mutations are identified by comparing tumor and normal genome sequences. Mutations can arise from missense mutations or an insertion/deletion. Genes with mutations are translated to the protein sequence which is then screened in silico using an algorithm (e.g. NetMHC, NetMHCpan, MHCFlurry, IEDB) that can predict peptide sequences likely to bind to patient HLA. From these algorithms, peptides are selected based on their affinity for MHC binding, whether they are naturally processed and presented and prediction of mutation functional impact using in silico algorithm (e.g. SIFT, POLYPHEN). Peptides are sequenced by a contract manufacturer under GMP conditions.

ii) Formulation in DepoVax (DPX)

To prepare vaccines, peptide mixture and adjuvants are first reconstituted in an appropriate aqueous buffer (e.g. acetate buffer, sodium phosphate, sodium bicarbonate, phosphate buffered saline) with DOPC and cholesterol (Lipoid, Germany). This preparation is then lyophilized to form a dry cake. Just prior to injection, the dry cake is reconstituted in an oil (e.g. ISA51 VG). Extra vials are prepared for moisture analysis and reconstitution testing.

iii) Animal Testing

Since neoantigen vaccines are uniquely and individually prepared for each patient, they cannot be tested in advance using animal models. Instead, it is possible to perform proof-of-concept using neoantigens derived from murine tumors (e.g. MethA, B16F10, etc.).

iv) Clinical Testing

Patient specific neoantigen vaccines are prepared using the methods described herein and administered to patients with or without concurrent treatment with immune modulators, such as metronomic cyclophosphamide or checkpoint inhibitors. Immunogenicity is monitored using IFN-gamma ELISPOT assay with PBMCs isolated from patients at regular intervals throughout the study. Immunogenicity can also be monitored using custom peptide-MHC multimer reagents to stain cells for flow cytometry.

Example 2

Pathogen free, C57BL/6 VAF/Elite® Crl mice, 6-8 weeks of age, were purchased from Charles River Laboratories (St. Constant, PQ) and housed according to institutional guidelines with water and food ad libitum under filter controlled air circulation. The neoantigen Mut30 (PSKPSFQEFVD-WENVSPELNSTDQPFL; SEQ ID NO: 2) was identified from Castle 2012 and was synthesized by Genscript.

The immunogenicity of the Mut30 peptide prepared in either an oil-based formulation or an aqueous formulation was compared. The formulations contained a DNA or RNA based poly I:C molecule as an adjuvant.

To prepare the oil-based formulations, the Mut30 peptide, polyI:C adjuvant (DNA or RNA) and T-helper epitope (A16L peptide) were first reconstituted in an acetate buffer (0.1M, pH 9.5) with DOPC and cholesterol (Lipoid, Germany). The vaccine components were then lyophilized to form a dry cake. Just prior to injection, the dry cake was reconstituted in ISA51 VG oil (SEPPIC, France).

To prepare the aqueous-based formulations, the Mut30 peptide, polyI:C adjuvant (DNA or RNA) and T-helper epitope (A16L peptide) were formulated in 0.05M sodium acetate buffer at pH 10±1.

Mice in group 1 (n=6) were vaccinated with 100 microliters of an aqueous buffered formulation containing 100 micrograms of Mut30 neoantigen, 50 micrograms of A16L peptide and 40 micrograms of DNA-based poly I:C in 0.05M sodium acetate buffer at pH 6±1.

Mice in group 2 (n=6) were vaccinated with 100 microliters of an aqueous buffered formulation containing 100 micrograms of Mut30 neoantigen, 50 micrograms of A16L peptide and 40 micrograms of RNA-based poly I:C in 0.05M sodium acetate buffer at pH 6±1.

Mice in group 3 (n=6) were vaccinated with 100 microliters of an oil-based depot vaccine containing 100 micrograms of Mut30 neoantigen, 50 micrograms of A16L peptide, 40 micrograms of DNA-based poly I:C, 12 milligrams of DOPC and 1.2 milligrams of cholesterol.

Mice in group 4 (n=6) were vaccinated with 100 microliters of an oil-based depot vaccine containing 100 micrograms of Mut30 neoantigen, 50 micrograms of A16L peptide, 40 micrograms of RNA-based poly I:C, 12 milligrams of DOPC and 1.2 milligrams of cholesterol.

Mice in group 5 (n=1) were not vaccinated.

Eight days after vaccination, mice were terminated and spleens collected. Splenocytes were stimulated in an IFN-gamma ELISPOT plate (BD Biosciences) with syngeneic dendritic cells unloaded (background) or loaded with an irrelevant peptide (RAHYNIVTF; SEQ ID NO: 8) or Mut30 antigen. After 18 hours of culture, plates were developed and the number of spot forming units (SFU) counted using Immunospot Reader (C.T.L.). The results are shown in FIG. 1 as average response±SEM. Statistical analysis was performed by 2-way ANOVA with Bonferroni post test comparing group responses to Mut30 peptide: *p<0.05, ***p<0.001.

The results demonstrate that the oil-based depot forming vaccines generate statistically significant stronger immune responses to neoantigen peptide after a single immunization compared to aqueous, non-depot forming vaccine formulations with identical components.

Example 3

Pathogen free, C57BL/6 VAF/Elite® Crl mice, 6-8 weeks of age, were purchased from Charles River Laboratories (St. Constant, PQ) and housed according to institutional guidelines with water and food ad libitum under filter controlled air circulation. The neoantigen Mut30 (PSKPSFQEFVD- WENVSPELNSTDQPFL; SEQ ID NO: 2) was identified from Castle 2012 and synthesized by Genscript.

Oil-based depot vaccine formulations were prepared with Mut30 antigen at a higher (100 micrograms) and lower (50 micrograms) dose.

To prepare the oil-based formulations, the Mut30 peptide (low or high dose amount), polyI:C adjuvant (DNA or RNA) and T-helper epitope (A16L peptide) were first reconstituted in an acetate buffer (0.1M, pH 9.5) with DOPC and cholesterol (Lipoid, Germany). The vaccine components were then lyophilized to form a dry cake. Just prior to injection, the dry cake was reconstituted in ISA51 VG oil (SEPPIC, France).

Mice in group 1 (n=6) were vaccinated with 100 microliters of an oil-based depot vaccine containing 100 micrograms of Mut30 neoantigen, 50 micrograms of A16L peptide, 40 micrograms of DNA-based poly I:C, 12 milligrams of DOPC and 1.2 milligrams of cholesterol.

Mice in group 2 (n=6) were vaccinated with 100 microliters of an oil-based depot vaccine containing 100 micrograms of Mut30 neoantigen, 50 micrograms of A16L peptide, 40 micrograms of RNA-based poly I:C, 12 milligrams of DOPC and 1.2 milligrams of cholesterol.

Mice in group 3 (n=6) were vaccinated with 100 microliters of an oil-based depot vaccine containing 50 micrograms of Mut30 neoantigen, 50 micrograms of A16L peptide, 40 micrograms of DNA-based poly I:C, 12 milligrams of DOPC and 1.2 milligrams of cholesterol.

Mice in group 4 (n=6) were vaccinated with 100 microliters of an oil-based depot vaccine containing 50 micrograms of Mut30 neoantigen, 50 micrograms of A16L peptide, 40 micrograms of RNA-based poly I:C, 12 milligrams of DOPC and 1.2 milligrams of cholesterol.

Mice in group 5 (n=1) were not vaccinated.

Eight days after vaccination, mice were terminated and spleens collected. Splenocytes were stimulated in an IFN-gamma ELISPOT plate (BD Biosciences) with syngeneic dendritic cells unloaded (background) or loaded with an irrelevant peptide (RAHYNIVTF; SEQ ID NO: 8) or Mut30 neoantigen. After 18 hours of culture, plates were developed and the number of spot forming units (SFU) counted using Immunospot Reader (C.T.L.). The results are shown in FIG. 2 as average response±SEM. Statistical analysis was performed by 2-way ANOVA with Bonferroni post test comparing group responses to Mut30 peptide. No statistically significant difference was observed between groups comparing high (100 micrograms) and low (50 micrograms) doses of Mut30 neoantigen with both DNA-based poly I:C and RNA-based poly I:C.

The results demonstrate that the oil-based depot forming vaccines generate comparable immune responses to neoantigen peptide at high (100 micrograms) and lower (50 micrograms) dose of antigen after a single immunization.

Example 4

Pathogen free, C57BL/6NCrl mice, 6-8 weeks of age, were purchased from Charles River Laboratories (St. Constant, PQ) and housed according to institutional guidelines with water and food ad libitum under filter controlled air circulation. The neoantigen Mut30 (PSKPSFQEFVD-WENVSPELNSTDQPFL; SEQ ID NO: 2) was identified from Castle 2012 and was synthesized by Genscript.

Two oil-based formulations were prepared with a RNA or DNA based poly I:C molecule and were compared to an aqueous buffer vaccine containing RNA based poly I:C. The aqueous buffer vaccine was designed to mimic the formulation described in Castle 2012.

To prepare the oil-based formulations, the Mut30 peptide, polyI:C adjuvant (DNA or RNA) and T-helper epitope (A16L peptide) were first reconstituted in an acetate buffer (0.1M, pH 9.5) with DOPC and cholesterol (Lipoid, Germany). The vaccine components were then lyophilized to form a dry cake. Just prior to injection, the dry cake was reconstituted in ISA51 VG oil (SEPPIC, France).

To prepare the aqueous-based formulations, the Mut30 peptide and RNA-based polyI:C adjuvant were formulated in 0.1M phosphate buffered saline at pH 10.0±1.

Mice in group 1 (n=5) were vaccinated with 100 microliters of an aqueous buffered formulation containing 100 micrograms of Mut30 neoantigen and 100 micrograms of RNA-based poly I:C in 0.05M sodium acetate buffer at pH 6.0.

Mice in group 2 (n=5) were vaccinated with 100 microliters of an oil-based depot vaccine containing 50 micrograms of Mut30 neoantigen, 50 micrograms of A16L peptide, 40 micrograms of RNA-based poly I:C, 12 milligrams of DOPC and 1.2 milligrams of cholesterol.

Mice in group 3 (n=4) were vaccinated with 100 microliters of an oil-based depot vaccine containing 50 micrograms of Mut30 neoantigen, 50 micrograms of A16L peptide, 40 micrograms of DNA-based poly I:C, 12 milligrams of DOPC and 1.2 milligrams of cholesterol.

Mice in group 4 (n=1) were not vaccinated.

Eight days after vaccination, mice were terminated and spleens collected. Splenocytes were stimulated in an IFN-gamma ELISPOT plate (BD Biosciences) with syngeneic dendritic cells unloaded (background) or loaded with an irrelevant peptide (EGPRNQDWL; SEQ ID NO: 9) or Mut30 neoantigen. After 18 hours of culture, plates were developed and the number of spot forming units (SFU) counted using Immunospot Reader (C.T.L.). The results are shown in FIG. 3 as average response±SEM. Statistical analysis was performed by 2-way ANOVA with Bonferroni post test comparing group responses to Mut30 peptide, *p<0.05, ***p<0.001.

The results demonstrate that the oil-based depot forming vaccine generates stronger immune responses to neoantigen peptides after a single immunization compared to an aqueous, non-depot forming vaccine.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to encompass the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

As used herein, whether in the specification or the appended claims, the transitional terms "comprising", "including", "carrying", "having", "containing", "involving", and the like are to be understood as being inclusive or open-ended (i.e., to mean including but not limited to), and they do not exclude unrecited elements, materials or method steps. Only the transitional phrases "consisting of" and "consisting essentially of", respectively, are closed or semi-closed transitional phrases with respect to claims and exemplary embodiment paragraphs herein. The transitional phrase "consisting of" excludes any element, step, or ingredient which is not specifically recited. The transitional phrase "consisting essentially of" limits the scope to the specified elements, materials or steps and to those that do not materially affect the basic characteristic(s) of the invention disclosed and/or claimed herein.

REFERENCES

1) Agger, E. M.; Rosenkrands, I.; Olsen, A. W.; Hatch, G.; Williams, A.; Kritsch, C.; Lingnau, K.; von Gabain, A.; Andersen, C. S.; Korsholm, K. S.; Andersen, P. (2006) Protective immunity to tuberculosis with Ag85B-ESAT-6 in a synthetic cationic adjuvant system IC31, *Vaccine* 24(26), 5452-5460.
2) Alexopoulou, L.; Holt, A. C.; Medzhitov, R.; Flavell, R. A. (2001) Recognition of double-stranded RNA and activation of NF-κB by Toll-like receptor 3, *Nature* 413 (6857), 732-738.
3) Awasthi, A.; Mehrotra, S.; Bhakuni, V.; Dutta, G. P.; Levy, H. B.; Maheshwari, R. K. (1997) Poly ICLC enhances the antimalarial activity of chloroquine against multidrug-resistant Plasmodium yoelii nigeriensis in mice, *J. Interferon Cytokine Res.* 17(7), 419-423.
4) Banga, A. K. *Therapeutic Peptides and Proteins, Formulation, Processing and Delivery systems* (Lancaster, Pa.: Technomic Publishing Co., 1995).
5) Bever, C. T. Jr.; Salazar, A. M.; Neely, E.; Ferraraccio, B. E.; Rose, J. W.; McFarland H. F.; Levy, H. B.; McFarlin, D. E. (1986) Preliminary trial of poly ICLC in chronic progressive multiple sclerosis, *Neurology* 36(4), 494-498.
6) Bobst, A. M.; Langemeier, P. W.; Torrence, P. F.; De Clercq, E. (1981) Interferon Induction by Poly(inosinic acid).Poly(cytidylic acid) Segmented by Spin-Labels, *Biochemistry* 20(16), 4798-4803.
7) Brewer, K. D.; Lake, K.; Pelot, N.; Stanford, M. M.; DeBay, D. R.; Penwell, A.; Weir, G. M.; Karkada, M.; Mansour, M.; Bowen, C. V. (2014) Clearance of depot vaccine SPIO-labeled antigen and substrate visualized using MM, *Vaccine* 32(51), 6956-6962.
8) Bruce, W. R.; Meeker, B. E.; Valeriote, F. A. (1996) Comparison of the sensitivity of normal hematopoietic and transplanted lymphoma colony-forming cells to chemotherapeutic agents administered in vivo, *J. Natl. Cancer Inst.* 37(2), 233-245.
9) Cabner, B. A. (2011) Cancer Chemotherapy and Biotherapy: Principles and Practice, $5^{th}$ edition, Lippincott Williams & Wilkins, PA, USA.
10) Castle, J. C.; Kreiter, S.; Diekmann, J.; Lower, M.; van de Roemer, N.; de Graaf, J.; Selmi, A.; Diken, M.; Boegel, S.; Paret, C.; Koslowski, M.; Kuhn, A. N.; Britten, C. M.; Huber, C.; Türeci, O.; Sahin, U. (2012) Exploiting the mutanome for tumor vaccination, *Cancer Res.* 72(5), 1081-91.
11) Celis, E.; Ou, D.; Otvos, L. Jr. (1988) Recognition of hepatitis B surface antigen by human T lymphocytes. Proliferative and cytotoxic responses to a major antigenic determinant defined by synthetic peptides, *J. Immunol.* 140, 1808-1815.
12) Chong, P.; Zobrist, G.; Sia, C.; Loosmore, S.; Klein, M. (1992) Identification of T- and B-cell epitopes of the S2 and S3 subunits of pertussis toxin by use of synthetic peptides, *Infect Immun.* 60, 4640-4647.
13) Chirigos, M. A.; Schlick, E.; Ruffmann, R.; Budzynski, W.; Sinibaldi, P.; Gruys, E. (1985) Pharmacokinetic and therapeutic activity of polyinosinic-polycytidylic acid stabilized with poly-L-lysine in carboxymethylcellulose [poly(I,C)-LC], *J. Biol. Response Mod.* 4(6), 621-627.
14) Cohen, J. L.; Jao, J. Y.; Jusko, W. J. (1971) Pharmacokinetics of cyclophosphamide in man, *Br. J. Pharmacol.* 43(3), 677-680.
15) Coligan et al., ed. Current Protocols in Immunology, Wiley Interscience, 2007.
16) Cui, Z.; Qiu, F. (2006) Synthetic double-stranded RNA poly(I:C) as a potent peptide vaccine adjuvant: therapeutic activity against human cervical cancer in a rodent model, *Cancer Immunol. Immunother.* 55(10), 1267-1279.
17) D'Incalci, M.; Bolis, G.; Facchinetti, T.; Mangioni, C.; Morasca, L.; Morazzoni, P.; Salmona, M. (1979) Decreased half life of cyclophosphamide in patients under continual treatment, *Eur. J. Cancer* 15(1), 7-10.
18) de Clercq, E.; Hattori, M.; Ikehara, M. (1975) Antiviral activity of polynucleotides: copolymers of inosinic acid and N2-dimethylguanylic of 2-methylthioinosinic acid, *Nucleic Acids Res.* 2(1), 121-129.
19) de Clercq, E.; Torrence, P. F.; Stollar, B. D.; Hobbs, J.; Fukui, T.; Kakiuchi, N.; Ikehara, M. (1978) Interferon induction by a 2'-modified double-helical RNA, poly(2'-azido-2'-deoxyinosinic acid). polycytidylic acid, *Eur. J. Biochem.* 88(2), 341-349.
20) de Jonge, M. E.; Huitema, A. D. R.; Rodenhuis, S.; Beijnen, J. H. (2005) Clinical pharmacokinetics of cyclophosphamide, *Clin. Pharmacokinet.* 44(11), 1135-1164.
21) Demotz, S.; Lanzavecchia, A.; Eisel, U.; Niemann, H.; Widmann, C.; Corradin, G. P. (1989) Delineation of several DR-restricted epitopes in tetanus toxin, *J. Immunol.* 142, 394-402.
22) Diethelm-Okita, B. M.; Okita, D. K.; Banaszak, L.; Conti-Fine, B. M. (2000) Universal epitopes for human CD4+ cells on tetanus and diphtheria toxins, *J. Infect. Dis.* 181, 1001-1009.

23) Dong, L. W.; Kong, X. N.; Yan, H. X.; Yu, L. X.; Chen, L.; Yang, W.; Liu, Q.; Huang, D. D.; Wu, M. C.; Wang, H. Y. (2008) Signal regulatory protein alpha negatively regulates both TLR3 and cytoplasmic pathways in type I interferon induction, *Mol. Immunol.* 45(11), 3025-3035.

24) Droller, M. J. (1987) Immunotherapy of metastatic renal cell carcinoma with polyinosinic-polycytidylic acid, *J. Urol.* 137(2), 202-206.

25) Duan, F.; Duitama, J.; Al Seesi, S.; Ayres, C. M.; Corcelli, S. A.; Pawashe, A. P.; Blanchard, T.; McMahon, D.; Sidney, J.; Sette, A.; Baker, B. M.; Mandoiu, I. I.; Srivastava, P. K. (2014) Genomic and bioinformatic profiling of mutational neoepitopes reveals new rules to predict anticancer immunogenicity, *J. Exp. Med.* 211(11), 2231-48.

26) Durie, B. G.; Levy, H. B.; Voakes, J.; Jett, J. R.; Levine, A. S. (1985) Poly(I,C)-LC as an interferon inducer in refractory multiple myeloma, *J. Biol. Response Mod.* 4(5), 518-524.

27) Emmenegger, U.; Shaked, Y.; Man, S.; Bocci, G.; Spasojevic, I.; Francia, G.; Kouri, A.; Coke, R.; Cruz-Munoz, W.; Ludeman, S. M.; Colvin, O. M.; Kerbel, R. S. (2007) Pharmacodynamic and pharmacokinetic study of chronic low-dosemetronomiccyclophosphamide therapy in mice, *Mol. Cancer Ther.* 6, 2280-2289.

28) Emmenegger, U.; Francia, G.; Chow, A.; Shaked, Y.; Kouri, A.; Man, S.; Kerbel, R. S. (2011) Tumors that acquire resistance to low-dose metronomic cyclophosphamide retain sensitivity to maximum tolerated dose cyclophosphamide, *Neoplasia* 13(1), 40-48.

29) Frezard, F. (1999) Liposomes: from biophysics to the design of peptide vaccines, *Braz. J. Med. Bio. Res.* 32, 181-189.

30) Fujimura, T.; Nakagawa, S.; Ohtani, T.; Ito, Y.; Aiba, S. (2006) Inhibitory effect of the polyinosinic-polycytidylic acid/cationic liposome on the progression of murine B16F10 melanoma, *Eur. J. Immunol.* 36(12), 3371-3380.

31) Fukui, T.; Kakiuchi, N.; Ikehara, M. (1977) Polynucleotides. XLV Synthesis and properties of poly(2'-azido-2'-deoxyinosinic acid), *Nucleic Acids Res.* 4(8), 2629-2639.

32) Gowen, B. B.; Wong, M. H.; Jung, K. H.; Sanders, A. B.; Mitchell, W. M.; Alexopoulou, L.; Flavell, R. A.; Sidwell, R. W. (2007) TLR3 is essential for the induction of protective immunity against Punta Toro Virus infection by the double-stranded RNA (dsRNA), poly(I:C12U), but not Poly(I:C): differential recognition of synthetic dsRNA molecules, *J. Immunol.* 178(8), 5200-5208.

33) Greene, J. J.; Alderfer, J. L.; Tazawa, I.; Tazawa, S.; Ts'o, P. O.; O'Malley, J. A.; Carter, W. A. (1978) Interferon induction and its dependence on the primary and secondary structure of poly(inosinic acid).poly(cytidylic acid), *Biochemistry* 17(20), 4214-4220.

34) Gregoriadis G. (1990) Immunological adjuvants: a role for liposomes, *Immunol. Today* 11, 89-97.

35) Guschlbauer, W.; Blandin, M.; Drocourt, J. L.; Thang, M. N. (1977) Poly-2'-deoxy-2'-fluoro-cytidylic acid: enzymatic synthesis, spectroscopic characterization and interaction with poly-inosinic acid, *Nucleic Acids Res.* 4(6), 1933-1943.

36) Hendrix, C. W.; Margolick, J. B.; Petty, B. G.; Markham, R. B.; Nerhood, L.; Farzadegan, H.; Ts'o, P. O.; Lietman, P. S. (1993) Biologic effects after a single dose of poly (I):poly(C12U) in healthy volunteers, *Antimicrob. Agents Chemother.* 37(3), 429-435.

37) Horn, T.; Vasser, M. P.; Struble, M. E.; Crea, R. (1980) Synthesis of oligonucleotides on cellulose. Part II: Design and synthetic strategy to the synthesis of 22 oligodeoxynucleotides coding for gastric inhibitory polypeptide (GIP), *Nucleic Acids Symp. Ser.* (7), 225-232.

38) Houston, W. E.; Crabbs, C. L.; Stephen, E. L.; Levy, H. B. (1976) Modified polyriboinosinic-polyribocytidylic acid, an immunological adjuvant, *Infect. Immun.* 14(1), 318-319.

39) Ichinohe, T.; Tamura, S.; Kawaguchi, A.; Ninomiya, A.; Imai, M.; Itamura, S.; Odagiri, T.; Tashiro, M.; Takahashi, H.; Sawa, H.; Mitchell, W. M.; Strayer, D. R.; Carter, W. A.; Chiba, J.; Kurata, T.; Sata, T.; Hasegawa, H. (2007) Cross-protection against H5N1 influenza virus infection is afforded by intranasal inoculation with seasonal trivalent inactivated influenza vaccine, *J. Infect. Dis.* 196(9), 1313-1320.

40) Irvine D J, Swartz M A, Szeto G L. Engineering synthetic vaccines using cues from natural immunity. Nat Mater. 2013 November; 12(11):978-90. doi: 10.1038/nmat3775.

41) Johnston, M. I.; Stollar, B. D.; Torrence, P. F.; Witkop, B. (1975) Structural features of double-stranded polyribonucleotides required for immunological specificity and interferon induction, *Proc. Natl. Acad. Sci. U.S.A.* 72(11), 4564-4568.

42) Juma, F. D., Rogers, H. J.; Trounce, J. R. (1979) Pharmacokinetics of cyclophosphamide and alkylating activity in man after intravenous and oral administration, *Br. J. Clin. Pharmacol.* 8(3), 209-217.

43) Kamath, A. T.; Valenti, M. P.; Rochat, A. F.; Agger, E. M.; Lingnau, K.; von Gabain, A.; Andersen, P.; Lambert, P. H.; Siegrist, C. A. (2008) Protective anti-mycobacterial T cell responses through exquisite in vivo activation of vaccine-targeted dendritic cells, *Eur. J. Immunol.* 38(5), 1247-1256.

44) Kende, M.; Lupton, H. W.; Rill, W. L.; Gibbs, P.; Levy, H. B.; Canonico, P. G. (1987) Ranking of Prophylactic Efficacy of Poly(ICLC) against Rift Valley Fever Virus Infection in Mice by Incremental Relative Risk of Death, *Antimicrob. Agents Chemother.* 31(8), 1194-1198.

45) Kim R, Emi M, Tanabe K. Cancer immunoediting from immune surveillance to immune escape. Immunology. 2007 May; 121(1):1-14. Epub 2007 Mar. 26.

46) Kreuter, J., ed. (1994), Colloidal Drug Delivery Systems, Vol. 66, Marcel Dekker, Inc.

47) Krown, S. E.; Kerr, D.; Stewart, W. E. 2nd; Field, A. K.; Oettgen, H. F. (1985) Phase I trials of poly(I,C) complexes in advanced cancer, *J. Biol. Response Mod.* 4(6), 640-649.

48) Levy, H. B. (1985) Historical overview of the use of polynucleotides in cancer, *J. Biol. Response Mod.* 4(5), 475-480.

49) Levy, H. B; Lvovsky, E. (1978) Topical treatment of vaccinia virus infection with an interferon inducer in rabbits, *J. Infect. Dis.* 137(1), 78-81.

50) Llopiz, D.; Dotor, J.; Zabaleta, A.; Lasarte, J. J.; Prieto, J.; Borrás-Cuesta, F.; Sarobe, P. (2008) Combined immunization with adjuvant molecules poly(I:C) and anti-CD40 plus a tumor antigen has potent prophylactic and therapeutic antitumor effects, *Cancer Immunol. Immunother.* 57(1), 19-29.

51) Merrifield, B. (1997) Concept and early development of solid-phase peptide synthesis, *Methods Enzymol.* 289, 3-13.

52) Mouridsen, H. T.; Faber, O.; Skovsted, L. (1974) The biotransformation of cyclophosphamide in man: analysis of the variation in normal subjects, *Acta Pharmacol. Toxicol. (Copenh)* 35(2), 98-106.

53) Moyle, P. M.; Toth. I. (2008) Self-adjuvanting lipopeptide vaccines, *Curr. Med. Chem.* 15(5), 506-516.

54) Mullard, A. (2016) The cancer vaccine resurgence, *Nat Rev Drug Disc* 15(10):663-665.

55) Nakamura, O.; shitara, N.; Matsutani, M.; Takakura, K.; Machida, H. (1982) Phase I-II trials of poly(ICLC) in malignant brain tumor patients, *J Interferon. Res.* 2(1), 1-4.

56) Padalko, E.; Nuyens, D.; De Palma, A.; Verbeken, E.; Aerts, J. L.; De Clercq, E.; Carmeliet, P.; Neyts, J. (2004) The Interferon Inducer Ampligen [poly(I)-poly($C_{12}$U)] Markedly Protects Mice against Coxsackie B3 Virus-Induced Myocarditis, *Antimicrob. Agents Chemother.* 48(1), 267-274.

57) Poast, J.; Seidel, H. M.; Hendricks, M. D.; Haslam, J. A.; Levy, H. B.; Baron, S. (2002) Poly I:CLC induction of the interferon system in mice: an initial study of four detection methods, *J. Interferon Cytokine Res.* 22(10), 1035-1040.

58) Puri, S. K.; Dutta, G. P.; Levy, H. B.; Maheshwari, R. K. (1996) Poly ICLC inhibits Plasmodium cynomolgi B malaria infection in rhesus monkeys, *J. Interferon. Cytokine Res.* 16(1), 49-52.

59) Reagan-Shaw, S.; Nihal, M.; Ahmad, N. (2008) Dose translation from animal to human studies revisited, *FASEB J.*, 22(3), 659-661.

60) Remington's Pharmaceutical Sciences, Mack Publishing Company, Easton, Pa., USA 1985

61) Riedl, K.; Riedl, R.; von Gabain, A.; Nagy, E.; Lingnau, K. (2008) The novel adjuvant IC31® strongly improves influenza vaccine-specific cellular and humoral immune responses in young adult and aged mice, *Vaccine* 26(27-28), 3461-3468.

62) Roberge, J. Y.; Beebe, X.; Danishefsky, S. J. (1995) A strategy for a convergent synthesis of N-linked glycopeptides on a solid support, *Science* 269(5221), 202-204.

63) Salazar, A. M.; Levy, H. B.; Ondra, S.; Kende, M.; Scherokman, B.; Brown, D.; Mena, H.; Martin, N.; Schwab, K.; Donovan, D.; Dougherty, D.; Pulliam, M.; Ippolito, M.; Graves, M.; Brown, H.; Ommaya, A. (1996) Long-term treatment of malignant gliomas with intramuscularly administered polyinosinic-polycytidylic acid stabilized with polylysine and carboxymethylcellulose: an open pilot study, *Neurosurgery* 38(6), 1096-1103, discussion at 1103-1104.

64) Salem, M. L.; Kadima, A. N.; Cole, D. J.; Gillanders, W. E. (2005) Defining the antigen-specific T-cell response to vaccination and poly(I:C)/TLR3 signaling: evidence of enhanced primary and memory CD8 T-cell responses and antitumor immunity, *J. Immunother.* 28(3), 220-228.

65) Salem, M. L.; El-Naggar, S. A.; Kadima, A.; Gillanders, W. E.; Cole, D. J. (2006) The adjuvant effects of the toll-like receptor 3 ligand polyinosinic-cytidylic acid poly (I:C) on antigen-specific CD8+ T cell responses are partially dependent on NK cells with the induction of a beneficial cytokine milieu, *Vaccine* 24(24), 5119-5132.

66) Sarma, P. S.; Shiu, G.; Neubauer, R. H.; Baron, S.; Huebner, R. J. (1969) Virus-induced sarcoma of mice: inhibition by a synthetic polyribonucleotide complex, *Proc. Natl. Acad. Sci. U.S.A.* 62(4), 1046-1051.

67) Schellack, C.; Prinz, K.; Egyed, A.; Fritz, J. H.; Wittmann, B.; Ginzler, M.; Swatosch, G.; Zauner, W.; Kast, C.; Akira, S.; von Gabain, A.; Buschle, M.; Lingnau, K. (2006) IC31, a novel adjuvant signaling via TLR9, induces potent cellular and humoral immune responses, *Vaccine* 24(26), 5461-5472.

68) Schumacher, T. N.; Schreiber, R. D. (2015) Neoantigens in cancer immunotherapy, *Science* 348(6230), 69-74.

69) Slingluff, C. L. Jr.; Yamshchikov, G.; Neese, P.; Galavotti, H.; Eastham, S.; Engelhard, V. H.; Kittlesen, D.; Deacon, D.; Hibbitts, S.; Grosh, W. W.; Petroni, G.; Cohen, R.; Wiernasz, C.; Patterson, J. W.; Conway, B. P.; Ross, W. G. (2001) Phase I trial of a melanoma vaccine with gp100(280-288) peptide and tetanus helper peptide in adjuvant: Immunologic and clinical outcomes, *Clin Cancer Res.* 7, 3012-3024.

70) Sloat, B. R.; Shaker, D. S.; Le, U. M.; Cui, Z. (2008) Nasal immunization with the mixture of PA63, LF, and a PGA conjugate induced strong antibody responses against all three antigens, *FEMS Immunol. Med. Microbiol.* 52(2), 169-179.

71) Smith, P. C.; Sladek, N. E. (1985) Sensitivity of murine B- and T-lymphocytes to oxazaphosphorine and non-oxazaphosphorine nitrogen mustards, *Biochem. Pharmacol.* 34(19), 3459-3463.

72) So, N. S. Y.; Ostrowski, M. A.; Gray-Owen, S. D. (2012) Vigorous Response of Human Innate Functioning IgM Memory B Cells upon Infection by *Neisseria gonorrhoeae*, *J. Immunol.* 188(8), 4008-4022.

73) Srivastava, P. (2015) Neoepitopes of Cancers: Looking Back, Looking Ahead, *Cancer Immunol. Res.* 3, 969-977.

74) Stephen, E. L.; Sammons, M. L.; Pannier, W. L.; Baron, S.; Spertzel, R. O.; Levy, H. B. (1977) Effect of a nuclease-resistant derivative of polyriboinosinic-polyribocytidylic acid complex on yellow fever in rhesus monkeys (*Macaca mulatta*), *J. Infect. Dis.* 136(1), 122-126.

75) Talmadge, J. E.; Adams, J.; Phillips, H.; Collins, M.; Lenz, B.; Schneider, M.; Chirigos, M. (1985) Immunotherapeutic potential in murine tumor models of polyinosinic-polycytidylic acid and poly-L-lysine solubilized by carboxymethylcellulose, *Cancer Res.* 45(3), 1066-1072.

76) The United States Pharmacopoeia: The National Formulary (USP 24 NF19) published in 1999

77) Theriault, R. L.; Hortobagyi, G. N.; Buzdar, A. U.; Levy, H. B.; Hersh, E. M. (1986) Evaluation of polyinosinic-polycytidylic and poly-L-lysine in metastatic breast cancer, *Cancer Treat. Rep.* 70(11), 1341-1342.

78) Trumpfheller, C.; Caskey, M.; Nchinda, G.; Longhi, M. P.; Mizenina, O.; Huang, Y.; Schlesinger. S. J.; Colonna, M.; Steinman, R. M. (2008) The microbial mimic poly IC induces durable and protective CD4+ T cell immunity together with a dendritic cell targeted vaccine, *Proc. Natl. Acad. Sci. U.S.A.* 105(7), 2574-2579.

79) Yoneyama, M.; Kikuchi, M.; Natsukawa, T.; Shinobu, N.; Imaizumi, T.; Miyagishi, M.; Taira, K.; Akira, S.; Fujita, T. (2004) The RNA helicase RIG-I has an essential function in double-stranded RNA-induced innate antiviral responses, *Nat. Immunol.* 5(7), 730-737.

80) Zaks, K.; Jordan, M.; Guth, A.; Sellins, K.; Kedl, R.; Izzo, A.; Bosio, C.; Dow, S. (2006) Efficient immunization and cross-priming by vaccine adjuvants containing TLR3 or TLR9 agonists complexed to cationic liposomes, *J. Immunol.* 176(12), 7335-7345.

81) Zhang, J.; Tian, Q.; Yung Chan, S.; Chuen Li, S.; Zhou, S.; Duan, W.; Zhu, Y. Z. (2005) Metabolism and transport of oxazaphosporines and the clinical implications, *Drug. Metab. Rev.* 37(4), 611-703.

82) Zhao, J.; Cao, Y.; Lei, Z.; Yang, Z.; Zhang, B.; Huang, B. (2010) Selective depletion of CD4+CD25+Foxp3+ regulatory T cells by low-dose cyclophosphamide is explained by reduced intracellular ATP levels, *Cancer Res.* 70(12), 4850-4858.

83) Zhu, X.; Nishimura, F.; Sasaki, K.; Fujita, M.; Dusak, J. E.; Eguchi, J.; Fellows-Mayle, W.; Storkus, W. J.; Walker, P. R.; Salazar, A. M.; Okada, H. (2007) Toll like receptor-3 ligand poly-ICLC promotes the efficacy of peripheral vaccinations with tumor antigen-derived peptide epitopes in murine CNS tumor models, *J. Transl. Med.* 5(10), 1-15.

The invention claimed is:

1. A vaccine composition comprising:
   (a) a lipid molecule mixture of 1,2-dioleoyl-sn-glycero-3-phosphocholine (DOPC) and cholesterol;
   (b) a neoantigen;
   (c) mannide oleate in mineral oil solution;
   (d) a T-helper epitope; and
   (e) a polyI:C polynucleotide adjuvant, wherein the composition is water-free or substantially free of water, wherein substantially free of water comprises less than about 10% water on a weight/weight basis of the total weight of the carrier, wherein the composition generates an enhanced cell-mediated immune response that is at least 2-fold greater than when the neoantigen is formulated in an aqueous-based vaccine formulation, and wherein the enhanced cell-mediated immune response is provided by only a single immunization with the composition.

2. The composition of claim 1, wherein a composition that is substantially free of water comprises less than about 9%, 8%, 7%, 6%, 5%, 4%, 3%, 2%, 1%, 0.5%, 0.1%, 0.05% or 0.01% water on a weight/weight basis of the total weight of the carrier.

3. The composition of claim 1, wherein the neoantigen is a neoantigenic peptide or a polynucleotide encoding a neoantigenic peptide.

4. The composition of claim 3, wherein the neoantigenic peptide is 5 to 50 amino acids in length.

5. The composition of claim 3, wherein the neoantigenic peptide comprises one or more neoepitopes.

6. The composition of claim 5, wherein the one or more neoepitopes are selected from: an MHC class I T-cell neoepitope of 9 to 11 amino acids in length; an MHC class II T-cell neoepitope of 13 to 17 amino acids in length; or a B-cell neoepitope of 5 to 20 amino acids in length.

7. The composition of claim 1, wherein the neoantigen comprises the amino acid sequence PSKPSFQEFVDWENVSPELNSTDQPFL (SEQ ID NO: 2).

8. The composition of claim 1, wherein the neoantigen is a weakly immunogenic antigen.

9. The composition of claim 1, wherein the composition comprises a low dose amount of the neoantigen.

10. The composition of claim 1, wherein the neoantigen is sufficiently hydrophobic, or is made sufficiently hydrophobic, such that the neoantigen is miscible in the hydrophobic carrier.

11. The composition of claim 10, wherein the neoantigen is made sufficiently hydrophobic by the presence of the amphipathic compound, wherein:
   the amphipathic compound is closely associated with the neoantigen to make the neoantigen miscible in the hydrophobic carrier; and/or
   the amphipathic compound forms a sheet or vesicular structure, partially or completely surrounding the neoantigen.

12. The composition of claim 1, wherein the T-helper epitope is PADRE comprising the amino acid sequence AKXVAAWTLKAAA (SEQ ID NO: 6); Tetanus toxoid peptide F21E comprising the amino acid sequence FNNFTVSFWLRVPKVSASHLE (SEQ ID NO: 7); or modified Tetanus toxin peptide A16L comprising the amino acid sequence AQYIKANSKFIGITEL (SEQ ID NO: 1).

13. The composition of claim 1, wherein the T-helper epitope is
   a universal T-helper epitope from tetanus toxoid comprising the amino acid sequence AQYIKANSKFIGITEL (SEQ ID NO: 1).

14. The composition of claim 1, which generates an enhanced cell-mediated immune response that is at least 3-fold, at least 4-fold, at least 5-fold, at least 6-fold, at least 7-fold, at least 8-fold, at least 9-fold or at least 10-fold greater than when the neoantigen is formulated in an aqueous-based vaccine formulation.

15. The composition of claim 14, wherein the enhanced cell-mediated immune response is provided by a low dose amount of the neoantigen in the composition, wherein the low dose amount is about 50% of the dose amount in the aqueous-based vaccine formulation.

16. A method for inducing an antibody immune response and/or a cell-mediated immune response to a neoantigen, said method comprising administering the composition of claim 1 to a subject in need thereof.

17. The method of claim 16 which comprises only a single administration of the composition to the subject.

18. The method of claim 16, wherein the composition comprises a low dose amount of the neoantigen.

19. The method according to claim 16, which is a method for the treatment and/or prevention of cancer.

20. The method according to claim 16, which further comprises administering to the subject an agent that interferes with DNA replication and/or an immune response checkpoint inhibitor.

21. The method according to claim 20, wherein the agent that interferes with DNA replication is cyclophosphamide and the immune response checkpoint inhibitor is an inhibitor of Programmed Death-Ligand 1 (PD-L1), Programmed Death 1 (PD-1), CTLA-4, PD-L2, LAG3, TIM3, 41BB, 2B4, A2aR, B7H1, B7H3, B7H4, BTLA, CD2, CD27, CD28, CD30, CD40, CD70, CD80, CD86, CD160, CD226, CD276, DR3, GAL9, GITR, HVEM, IDO1, IDO2, inducible T cell costimulatory (ICOS), KIR, LAIR1, LIGHT, macrophage receptor with collageneous structure (MARCO), phosphatidylserine (PS), OX-40, SLAM, TIGIT, VISTA, VTCN1, or any combination thereof.

22. A kit comprising:
   a first container comprising a lipid molecule mixture of 1,2-dioleoyl-sn-glycero-3-phosphocholine (DOPC) and cholesterol, a T-helper epitope, a polyI:C polynucleotide adjuvant, and a neoantigen; and
   a second container comprising mannide oleate in mineral oil solution.

* * * * *